USO12239529B2

(12) United States Patent
Faria Ribeiro et al.

(10) Patent No.: US 12,239,529 B2
(45) Date of Patent: Mar. 4, 2025

(54) REFRACTIVE EXTENDED DEPTH OF FOCUS INTRAOCULAR LENS, AND METHODS OF USE AND MANUFACTURE

(71) Applicant: AMO Groningen B.V., Groningen (NL)

(72) Inventors: Miguel Faria Ribeiro, Braga (PT); Franck Gounou, Groningen (NL); Carmen Canovas Vidal, Groningen (NL); Aixa Alarcon Heredia, Haren (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 17/653,646

(22) Filed: Mar. 5, 2022

(65) Prior Publication Data
US 2022/0287825 A1 Sep. 15, 2022

Related U.S. Application Data

(60) Provisional application No. 63/158,860, filed on Mar. 9, 2021.

(51) Int. Cl.
*A61F 2/16* (2006.01)
*G02C 7/02* (2006.01)

(52) U.S. Cl.
CPC ............ *A61F 2/1618* (2013.01); *G02C 7/028* (2013.01)

(58) Field of Classification Search
CPC ......... A61F 2/1618; A61F 2/16; G02C 7/028; G02C 7/042; G02C 7/044
See application file for complete search history.

(56) References Cited

U.S. PATENT DOCUMENTS

| RE32,525 E | 10/1987 | Pannu |
| 5,050,981 A | 9/1991 | Roffman |
| 5,112,351 A | 5/1992 | Christie et al. |
| 5,220,359 A | 6/1993 | Roffman |

(Continued)

FOREIGN PATENT DOCUMENTS

| AU | 2010212408 A1 | 9/2010 |
| AU | 2005230194 B2 | 12/2010 |

(Continued)

OTHER PUBLICATIONS

Alarcon A., et al., "Preclinical Metrics to Predict through-focus Visual Acuity for Pseudophakic Patients," Biomedical Optics Express, 2016, vol. 7 (5), pp. 1877-1888.

(Continued)

*Primary Examiner* — Melanie R Tyson
*Assistant Examiner* — Yasniary De La Caridad Morales

(57) ABSTRACT

Apparatuses, systems, and methods for providing improved intraocular lenses (IOLs) and other refractive treatment modalities involve fabricating the IOL or developing the treatment based on a refractive profile. Exemplary techniques include obtaining a base wavefront power profile corresponding to a theoretical lens, adding a second wavefront profile defined by the combination of one or more zones described by a cosine function to obtain a final wavefront power profile, determining a refractive profile based on the final wavefront power profile, and fabricating the intraocular lens or determining the treatment based on the refractive profile.

9 Claims, 22 Drawing Sheets

(56) References Cited

U.S. PATENT DOCUMENTS

| | | | |
|---|---|---|---|
| 5,448,312 A | 9/1995 | Roffman et al. | |
| 5,485,228 A | 1/1996 | Roffman et al. | |
| 5,652,638 A | 7/1997 | Roffman et al. | |
| 5,682,223 A | 10/1997 | Menezes et al. | |
| 5,684,560 A | 11/1997 | Roffman et al. | |
| 5,702,440 A | 12/1997 | Portney | |
| 5,715,031 A | 2/1998 | Roffman et al. | |
| 5,724,258 A | 3/1998 | Roffman | |
| 5,760,871 A | 6/1998 | Kosoburd et al. | |
| 5,796,462 A | 8/1998 | Roffman et al. | |
| 5,805,260 A | 9/1998 | Roffman et al. | |
| 5,847,802 A | 12/1998 | Menezes et al. | |
| 5,864,378 A | 1/1999 | Portney | |
| 5,919,229 A | 7/1999 | Portney | |
| 5,929,969 A | 7/1999 | Roffman | |
| 6,024,447 A | 2/2000 | Portney | |
| 6,086,203 A | 7/2000 | Blum et al. | |
| 6,106,118 A | 8/2000 | Menezes et al. | |
| 6,511,178 B1 | 1/2003 | Roffman et al. | |
| 6,520,638 B1 | 2/2003 | Roffman et al. | |
| 6,527,389 B2 | 3/2003 | Portney | |
| 6,537,317 B1 | 3/2003 | Steinert et al. | |
| 6,547,391 B2 | 4/2003 | Ross, III et al. | |
| 6,547,822 B1 | 4/2003 | Lang | |
| 6,554,425 B1 | 4/2003 | Roffman et al. | |
| 6,554,859 B1 | 4/2003 | Lang et al. | |
| 6,576,011 B2 | 6/2003 | Portney | |
| 6,576,012 B2 | 6/2003 | Lang | |
| 6,582,076 B1 | 6/2003 | Roffman et al. | |
| 6,598,606 B2 | 7/2003 | Terwee et al. | |
| 6,609,793 B2 | 8/2003 | Norrby et al. | |
| 6,638,305 B2 | 10/2003 | Laguette | |
| 6,705,729 B2 | 3/2004 | Piers et al. | |
| 6,709,103 B1 | 3/2004 | Roffman et al. | |
| 6,830,332 B2 | 12/2004 | Piers et al. | |
| 6,899,425 B2 | 5/2005 | Roffman et al. | |
| 6,986,578 B2 | 1/2006 | Jones | |
| 7,018,409 B2 | 3/2006 | Glick et al. | |
| 7,048,759 B2 | 5/2006 | Bogaert et al. | |
| 7,137,702 B2 | 11/2006 | Piers et al. | |
| 7,150,759 B2 | 12/2006 | Paul et al. | |
| 7,188,949 B2 | 3/2007 | Bandhauer et al. | |
| 7,241,311 B2 | 7/2007 | Norrby et al. | |
| 7,370,962 B2 | 5/2008 | Roffman et al. | |
| 7,377,640 B2 | 5/2008 | Piers et al. | |
| 7,377,641 B2 | 5/2008 | Piers et al. | |
| 7,381,221 B2 | 6/2008 | Lang et al. | |
| 7,441,894 B2 | 10/2008 | Zhang et al. | |
| 7,455,404 B2 | 11/2008 | Bandhauer et al. | |
| 7,455,407 B2 | 11/2008 | Neal et al. | |
| 7,475,986 B2 | 1/2009 | Dai et al. | |
| 7,543,937 B2 | 6/2009 | Piers et al. | |
| 7,615,073 B2 | 11/2009 | Deacon et al. | |
| 7,616,330 B2 | 11/2009 | Neal et al. | |
| 7,670,371 B2 | 3/2010 | Piers et al. | |
| 7,677,725 B2 | 3/2010 | Piers et al. | |
| 7,713,299 B2 | 5/2010 | Brady et al. | |
| 7,753,521 B2 | 7/2010 | Wooley et al. | |
| 7,794,497 B2 | 9/2010 | Brady et al. | |
| 7,871,162 B2 | 1/2011 | Weeber | |
| 7,896,916 B2 | 3/2011 | Piers et al. | |
| 7,922,326 B2 | 4/2011 | Bandhauer et al. | |
| 7,984,990 B2 | 7/2011 | Bandhauer et al. | |
| 7,993,398 B2 | 8/2011 | Deacon et al. | |
| 8,002,827 B2 | 8/2011 | Deacon et al. | |
| 8,079,704 B2 | 12/2011 | Sanger | |
| 8,231,219 B2 | 7/2012 | Weeber | |
| 8,292,953 B2 | 10/2012 | Weeber et al. | |
| 8,382,281 B2 | 2/2013 | Weeber | |
| 8,430,508 B2 | 4/2013 | Weeber | |
| 8,444,267 B2 | 5/2013 | Weeber et al. | |
| 8,480,228 B2 | 7/2013 | Weeber | |
| 8,529,623 B2 | 9/2013 | Piers et al. | |
| 8,573,775 B2 | 11/2013 | Weeber | |
| 8,619,362 B2 | 12/2013 | Portney | |
| 8,696,746 B2 | 4/2014 | Wanders et al. | |
| 8,747,466 B2 | 6/2014 | Weeber et al. | |
| 8,862,447 B2 | 10/2014 | Weeber | |
| 8,974,526 B2 | 3/2015 | Bogaert | |
| 9,335,563 B2 | 5/2016 | Weeber | |
| 9,638,936 B2 | 5/2017 | Brennan et al. | |
| 9,968,440 B2 | 5/2018 | Hong et al. | |
| 10,028,825 B2 | 7/2018 | Canovas et al. | |
| 10,265,162 B2 | 4/2019 | Bogaert | |
| 10,359,646 B2 | 7/2019 | Brennan et al. | |
| 10,426,601 B2 | 10/2019 | Canovas Vidal et al. | |
| 10,564,448 B2 | 2/2020 | Ando | |
| 10,624,735 B2 | 4/2020 | Canovas Vidal et al. | |
| 10,709,550 B2 | 7/2020 | Canovas et al. | |
| 10,792,147 B2 | 10/2020 | Okudaira | |
| 10,823,980 B2 | 11/2020 | Brennan et al. | |
| 10,838,236 B2 | 11/2020 | Brennan et al. | |
| 10,871,659 B2 | 12/2020 | Hong et al. | |
| 11,000,362 B2 | 5/2021 | Canovas Vidal et al. | |
| 11,249,326 B2 | 2/2022 | Zhao | |
| 11,333,903 B2 | 5/2022 | Bakaraju et al. | |
| 2004/0111153 A1 | 6/2004 | Woods et al. | |
| 2004/0150790 A1 | 8/2004 | Roffman et al. | |
| 2004/0189981 A1 | 9/2004 | Ross et al. | |
| 2004/0230299 A1* | 11/2004 | Simpson | A61F 2/1613 623/6.11 |
| 2005/0068494 A1 | 3/2005 | Griffin | |
| 2005/0251254 A1 | 11/2005 | Brady et al. | |
| 2006/0055883 A1 | 3/2006 | Morris et al. | |
| 2006/0238702 A1 | 10/2006 | Glick et al. | |
| 2008/0018910 A1 | 1/2008 | Neal et al. | |
| 2008/0161914 A1 | 7/2008 | Brady et al. | |
| 2008/0291393 A1 | 11/2008 | Menezes | |
| 2009/0012609 A1 | 1/2009 | Geraghty et al. | |
| 2009/0036980 A1 | 2/2009 | Norrby et al. | |
| 2009/0062911 A1 | 3/2009 | Bogaert | |
| 2009/0210054 A1 | 8/2009 | Weeber et al. | |
| 2009/0234448 A1 | 9/2009 | Weeber et al. | |
| 2009/0323020 A1 | 12/2009 | Zhao et al. | |
| 2010/0082017 A1 | 4/2010 | Zickler et al. | |
| 2010/0100177 A1 | 4/2010 | Zhao | |
| 2010/0100178 A1 | 4/2010 | Weeber et al. | |
| 2010/0161051 A1 | 6/2010 | Hong | |
| 2010/0274234 A1 | 10/2010 | Liang | |
| 2010/0281021 A1 | 11/2010 | Weeber et al. | |
| 2010/0321632 A1* | 12/2010 | Sanger | G02C 7/028 351/159.41 |
| 2011/0109874 A1 | 5/2011 | Piers et al. | |
| 2011/0166652 A1 | 7/2011 | Bogaert et al. | |
| 2012/0059464 A1 | 3/2012 | Zhao | |
| 2012/0140166 A1 | 6/2012 | Zhao | |
| 2012/0143326 A1 | 6/2012 | Canovas et al. | |
| 2012/0320335 A1 | 12/2012 | Weeber et al. | |
| 2013/0060330 A1 | 3/2013 | Weeber et al. | |
| 2013/0090730 A1 | 4/2013 | Weeber et al. | |
| 2014/0009736 A1* | 1/2014 | Zhao | G02C 7/024 351/159.01 |
| 2016/0062144 A1 | 3/2016 | Brennan et al. | |
| 2016/0062145 A1 | 3/2016 | Brennan et al. | |
| 2016/0161364 A1 | 6/2016 | Alarcon Heredia et al. | |
| 2017/0115509 A1 | 4/2017 | Brennan et al. | |
| 2017/0216020 A1 | 8/2017 | Weeber et al. | |
| 2019/0004221 A1 | 1/2019 | Weeber et al. | |
| 2019/0247182 A1 | 8/2019 | Bogaert | |
| 2020/0022806 A1 | 1/2020 | Carmen et al. | |
| 2020/0330218 A1 | 10/2020 | Carmen et al. | |
| 2021/0063767 A1 | 3/2021 | Hong et al. | |
| 2021/0199989 A1 | 7/2021 | Rosen et al. | |
| 2022/0047384 A1 | 2/2022 | Canovas Vidal et al. | |

FOREIGN PATENT DOCUMENTS

| | | |
|---|---|---|
| CA | 2722274 A1 | 10/2009 |
| CA | 2787997 C | 2/2015 |
| CA | 2901889 A1 | 2/2016 |
| EP | 742466 A2 | 11/1996 |
| EP | 1376203 A2 | 1/2004 |
| EP | 1631217 A2 | 3/2006 |
| EP | 2043558 A2 | 4/2009 |

(56) References Cited

FOREIGN PATENT DOCUMENTS

| | | | |
|---|---|---|---|
| EP | 1402308 B1 | 5/2009 | |
| EP | 1424049 B1 | 6/2009 | |
| EP | 1381908 B1 | 8/2010 | |
| EP | 2365379 A1 | 9/2011 | |
| EP | 2363097 B1 | 9/2012 | |
| EP | 1149323 B1 | 5/2013 | |
| EP | 2358306 B1 | 10/2013 | |
| EP | 2646872 A1 | 10/2013 | |
| EP | 2182891 B1 | 4/2014 | |
| EP | 2988161 A1 | 2/2016 | |
| EP | 3052983 A1 | 8/2016 | |
| EP | 2403429 B1 | 2/2017 | |
| EP | 3336600 A1 | 6/2018 | |
| EP | 3413839 A1 | 12/2018 | |
| EP | 3413840 A1 | 12/2018 | |
| EP | 3413841 A1 | 12/2018 | |
| EP | 2527908 B1 | 3/2019 | |
| EP | 3514613 A1 | 7/2019 | |
| EP | 3667402 A1 | 6/2020 | |
| EP | 2988162 B1 | 7/2020 | |
| EP | 3958045 A1 * | 2/2022 | ........... A61F 2/1618 |
| EP | 3973353 A1 | 3/2022 | |
| JP | 2004537332 A | 12/2004 | |
| WO | 0111418 A1 | 2/2001 | |
| WO | 0221194 A2 | 3/2002 | |
| WO | 0234158 A2 | 5/2002 | |
| WO | 02084381 A3 | 10/2003 | |
| WO | 2004049979 A1 | 6/2004 | |
| WO | 2006047698 A1 | 5/2006 | |
| WO | 2008083283 A2 | 7/2008 | |
| WO | WO-2008078804 A1 * | 7/2008 | ........... A61F 2/1618 |
| WO | 2009027438 A2 | 3/2009 | |
| WO | 2009029515 A1 | 3/2009 | |
| WO | 2009076670 A1 | 6/2009 | |
| WO | 2010100523 A1 | 9/2010 | |
| WO | 2013028992 A1 | 2/2013 | |
| WO | 2014033543 A2 | 3/2014 | |
| WO | 2017137839 A1 | 8/2017 | |
| WO | 2017137840 A1 | 8/2017 | |
| WO | 2020236330 A1 | 11/2020 | |
| WO | 2021240465 A2 | 12/2021 | |

OTHER PUBLICATIONS

Norrby S., et al., "Model Eyes for Evaluation of Intraocular Lenses," Applied Optics, Sep. 7, 2007, vol. 46 (26), pp. 6595-6605.

Piers P.A., et al., "Eye Models for the Prediction of Contrast Vision in Patients with New Intraocular Lens Designs," Optics Letters, Apr. 1, 2004, vol. 29 (7), pp. 733-735.

Piers P.A., et al., "Theoretical Comparison of Aberration-Correcting Customized and Aspheric Intraocular Lenses," Journal of Refractive Surgery, Apr. 2007, vol. 23 (4), pp. 374-384.

* cited by examiner

Initial

Intermediate

Final

Small Pupil

PPT p.1

PPT p.1

PPT p.2

REFRACTIVE EXTENDED DEPTH OF FOCUS INTRAOCULAR LENS, AND METHODS OF USE AND MANUFACTURE

CROSS REFERENCE TO RELATED APPLICATIONS

This application claims priority to U.S. Provisional Patent Application No. 63/158,860, filed on Mar. 9, 2021, the entire contents of which are hereby incorporated by reference.

BACKGROUND OF THE INVENTION

Embodiments of the present invention relate generally to lens characteristics, and particular embodiments provide methods, devices, and systems for mitigating or treating vision conditions such as presbyopia, often by determining a dioptric power profile of a wavefront that emerges from an intraocular lens and determining a surface feature of the lens based on the dioptric power profile.

In multifocal intraocular lenses (IOLs), multiple optical zones provide for different optical powers at the different zones. The multiple optical zones can improve the vision of a patient at different viewing distances, such as near distance, intermediate distance, and far distance. Therefore, an implanted intraocular lens with multiple zones can allow a patient to see with improved acuity at multiple viewing distances. However, multifocal intraocular lenses can also reduce the contrast on the image and can increase night vision disturbances such as glare and halo. Moreover, multifocal IOLs can also cause the best focus shift under different light conditions.

Although current and proposed multifocal intraocular lenses and related methods provide real benefits to patients in need thereof, still, further advances would be desirable. Embodiments of the present invention provide solutions to at least some of these outstanding needs.

BRIEF SUMMARY OF THE INVENTION

Cataract surgery typically involves the removal of the natural lens of the eye and the placement of an intraocular lens (IOL) implant in its place. This implanted lens can either have a single focal point, only meant to correct vision at a single distance, or multiple focal points for distance, intermediate and near, which are commonly labeled presbyopia correcting IOLs (PCIOLs). The two main types PCIOLs include diffractive and/or refractive optical elements. While there are potential advantages provided by the diffractive elements, in terms of through-focus performance and improved spectacle independence, there are also downsides related with unwanted visual symptoms such as multiple halos and starburst, produced by the abrupt changes in the sagitta of the surface, associated with the repeating diffractive ring structure.

Refractive PCIOLs, on the other hand, might extend the depth of focus with reduced halo perception. By designing an optical surface with multiple zones of different curvature, light can be focused at multiple planes creating an extended focus. Each zone can be defined as a part of the optical surface defined between discrete radii from the center of the lens. Adjacent zones may tend to meet at abrupt changes in curvature. An abrupt optical power step between adjacent zones can cause visual artifacts including glare, halos, and decreased contrast sensitivity.

To obtain a continuous surface, without any abrupt changes in curvature, the different zones can be fitted with a high order polynomial. A problem with this approach is that the resulting surface sagitta deviates from the designed one when using complex multizonal designs, and so does its optical performance. For simpler surfaces with less than three different zones of different curvature, high order polynomials are still able produce an acceptable fit, but for more complicated designs high order polynomials may fail to represent low amplitude surface deformation patterns, commonly known as Runge's phenomenon. The suboptimal polynomial fit will result in a suboptimum through-focus performance, due to the lack of control over the final design produced by the fit and/or to the mathematical limitation of representing more complex shapes. Relatedly, visual artifacts are often perceived by patients treated with currently available multifocal IOLs, and are typically produced by point sources of light, such as automobile headlights and traffic or streetlights. Advantageously, IOL embodiments disclosed herein provide improved optical performance in low-light or night viewing conditions by avoiding or reducing side effects, including visual artifacts such as glare and halo, as well as best focus shifts and contrast sensitivity loss.

Embodiments of the present invention solve these and other problems by implementing surfaces that provide smooth phase transitions that are created by having optical powers that vary as a cosine function of the radial position inside zones of the wavefront. In some cases, embodiments encompass devices and methods where the phase of the lens is constructed as a series of cosine functions.

In one aspect, embodiments of the present invention encompass systems and methods for fabricating an intraocular lens. Exemplary methods can include obtaining a first wavefront power profile (base power profile) corresponding to a theoretical lens, adding to the first wavefront profile a second wavefront profile defined for one or more zones and delineated by a cosine function, thereby obtaining a final wavefront power profile, determining a refractive profile based on the final wavefront power profile, and fabricating the intraocular lens based on the refractive profile. In some cases, the second wavefront power profile includes a first zone, a second zone disposed peripherally to the first zone, and a third zone disposed peripherally to the second zone. In some cases, the second wavefront power profile comprises an optical power that varies as a cosine transformation of radial position inside each zone. This enables improved optical performance in low-light or night viewing conditions by avoiding or reducing side effects, including visual artifacts such as glare and halo, as well as best focus shifts and contrast sensitivity loss. In some cases, the cosine transformation operates to determine an optical power $P_k(r)$ that varies as a cosine function of radial position inside each of the first, second, and third zones, according to a profile defined by a formula as follows:

$$P_k(r) = S_k - A_k(-1)^{CosOrderk} * \left[ \frac{-1}{2} + \frac{1}{2}\cos\left[\pi\left[\frac{r^2 - rz_{ik}^2}{rz_{ek}^2 - rz_{ik}^2}\right]\right]^{CosOrderk} \right] \quad [1]$$

In some cases, $A_k$ is an amplitude that is defined as a difference between a starting and a final sagittal power within zone k, $S_k$ is a starting sagittal power of each zone, $rz_{ik}$ and $rz_{ek}$ are respectively starting (initial) and final radial coordinates of zone k (where the radii are defined, for example, with respect to the center of the lens or its optical axis), and CosOrderk defines the power exponent of the cosine function of zone k. $S_k$ can be defined as a constant value or as a variable function that depends on the radial coordinate, r, $S_k(r)$. In some cases, the amplitude A is provided in units of diopters. In some cases, the starting sagittal power is provided in units of diopters. In some cases, the starting and final radial coordinates are provided in units of mm. In some cases, the step of determining the refractive profile comprises: processing the final wavefront power profile with an analytical transformation to obtain the refractive profile. In some cases, the final wavefront power profile is continuous. In some cases, the refractive profile is continuous and differentiable. In some cases, the intraocular lens has a refractive shape that is based on the refractive profile. In some cases, the final wavefront profile has a relative sagittal power value of zero at a radial position of zero. In some cases, the final wavefront profile has a relative sagittal power value that is non-zero at a radial position of zero. In some cases, the relative sagittal power value is at the radial position of zero is negative. In some cases, the final wavefront power profile has a center near configuration. In some cases, the final wavefront power profile has a center distance configuration. In some cases, the intraocular lens comprises a diffractive shape. In some cases, the second wavefront power profile further comprises a fourth zone disposed peripherally to the third zone, a fourth zone disposed peripherally to the third zone and a fifth zone disposed peripherally to the fourth zone, or a fourth zone disposed peripherally to the third zone, a fifth zone disposed peripherally to the fourth zone, and a sixth zone disposed peripherally to the fifth zone. The total number of zones may be 2, 3, 4, 5, 6, 7, 8, 9 or 10, with respectively k in the range of 1-2, 1-3, 1-4, 1-5, 1-6, 1-7, 1-8, 1-9 or 1-10, without limitation. The above profile [1] further enables improved optical performance in low-light or night viewing conditions by avoiding or reducing side effects, including visual artifacts such as glare and halo, as well as best focus shifts and contrast sensitivity loss. This is achieved by having optical powers that vary as a cosine function of the radial position inside zones of the wavefront to provide smooth phase transitions.

In some cases, processing the final wavefront power profile with the analytical transformation may be achieved by finding the Optical Path Difference (OPD). An overall total power profile of the intraocular lens $P(r)$ can be defined as:

$$P(r)=P_k(r)+B(r)+P_{IOL}$$

In some cases, the first wavefront power profile can comprise a radially varying base profile, $B(r)$ and a constant intraocular lens base power, $P_{IOL}$. The total power of the intraocular lens, $P(r)$ can be decomposed into the power provided by the anterior surface and the power provided by the posterior surface. To obtain the new shape of the anterior (or posterior) surface of the lens, the contribution of the posterior (or anterior respectively) surface power is calculated and extracted from the total power of the intraocular lens, $P(r)$. For example, the power of the anterior surface of the lens can be calculated by ray-tracing and extracted from the total power of the intraocular lens to obtain the new posterior surface power, $P_{pos}(r)$.

The power of the posterior surface, $P_{pos}(r)$, can be converted into a refractive profile corresponding to an Optical Path Difference (OPD) as follows:

$$OPD(r)=\int P_{pos}(r)\cdot rdr$$

And this can be converted into lens shape using the equation:

$$DeltaOPD(\text{waves}) = \frac{DeltaSag(\text{mm}) * (RI_{lens} - RI_{aqueous})}{0.55}$$

Where $RI_{lens}$ is a refractive index value of the lens, $RI_{aqueous}$ is a refractive index value of the aqueous humor of the eye, DeltaOPD(waves) is the OPD provided above and DeltaSag (mm) is the shape of the posterior surface (also called elevation) of the intraocular lens. $RI_{aqueous}$ is typically in the range of 1.3 to 1.4, and specifically around 1.336, and the Mlens is defined by the material used to create the IOL, but may typically be in the range of 1.4 to 1.7.

According to some embodiments, each zone k is defined by a starting sagittal power ($S_k$), a final sagittal power, a starting radial position ($rz_{ik}$), and a final radial position of the zone ($rz_e$). In some cases, the starting radial position ($rz_{ik}$) of the first zone is zero. In some cases, the final wavefront profile has a relative sagittal power value of zero at least at one radial position and a relative sagittal power value that is positive with a value between 0.1 and 5 D for at least at one radial position. In some cases, the final wavefront profile has a relative sagittal power value that is negative (with a value between −0.05 and −2 D) at least at one radial position and a relative sagittal power value that is positive (with a value between 0.1 and 5 D) for at least at one radial position. In some cases, the sagittal power of the first zone is positive with at least one additional zone with zero or negative relative sagittal power. In some cases, the sagittal power of the first zone is zero or negative with at least one additional zone with positive relative sagittal power. In some cases, the optical power $P(r)$ profile is combined with a spherical intraocular lens design. In some cases, the optical power $P(r)$ profile is combined with an aspheric intraocular lens design corresponding to the first wavefront power profile (base power profile). In some cases, the optical power $P(r)$ profile is combined with an astigmatism correcting intraocular lens design. In some cases, the optical power $P(r)$ profile is combined with a diffractive profile.

In another aspect, embodiments of the present invention encompass computer systems and methods to generate a refractive shape for use in fabricating an intraocular lens. Exemplary computer systems can include a processor, an electronic storage location operatively coupled with the processor, and processor executable code stored on the electronic storage location and embodied in a tangible non-transitory computer readable medium. The processor executable code, when executed by the processor, can cause the processor to generate the refractive shape by obtaining a first wavefront power profile (base power profile) corresponding to a theoretical lens, adding to the first wavefront profile a second wavefront profile defined for one or more zones and delineated by a cosine function, thereby obtaining the final wavefront power profile, and determining the refractive profile based on the final wavefront power profile. In some cases, the second wavefront power profile includes a first zone, a second zone disposed peripherally to the first zone, and a third zone disposed peripherally to the second zone. In some cases, the second wavefront power profile comprises an optical power that varies as a cosine transformation of radial position inside each zone. This enables improved optical performance in low-light or night viewing conditions by avoiding or reducing side effects, including visual artifacts such as glare and halo, as well as best focus shifts and contrast sensitivity loss. In some cases, the cosine transformation operates to determine an optical power $P_k(r)$ that varies as a cosine function of radial position inside each of the first, second, and third zones, according to a profile defined by a formula as follows:

$$P_k(r) = S_k - A_k(-1)^{CosOrderk} * \left[\frac{-1}{2} + \frac{1}{2}\cos\left[\pi\left[\frac{r^2 - rz_{ik}^2}{rz_{ek}^2 - rz_{ik}^2}\right]\right]^{CosOrderk}\right] \quad [1]$$

In some cases, $A_k$ is an amplitude that is defined as a difference between a starting and a final sagittal power within zone k, $S_k$ is a starting sagittal power of each zone, $rz_{ik}$ and $rz_{ek}$ are respectively starting (initial) and final radial coordinates of each zone, k (where the radii are defined, for example, with respect to the center of the lens or its optical axis), and CosOrderk defines the power exponent of the cosine function. $S_k$ can be defined as a constant value or as a variable function that depends on the radial coordinate, r, $S_k(r)$. In some cases, the amplitude $A_k$ is provided in units of diopters. In some cases, the starting sagittal power is provided in units of diopters. In some cases, the starting and final radial coordinates are provided in units of mm. In some cases, the step of determining the refractive profile comprises processing the final wavefront power profile with an analytical transformation to obtain the refractive profile (see above). In some cases, the final wavefront power profile is continuous. In some cases, the refractive profile is continuous and differentiable. In some cases, the intraocular lens has a refractive shape that is based on the refractive profile. In some cases, the final wavefront profile has a relative sagittal power value of zero at a radial position of zero. In some cases, the final wavefront profile has a relative sagittal power value that is non-zero at a radial position of zero. In some cases, the relative sagittal power value is at the radial position of zero is negative. In some cases, the final wavefront power profile has a center near configuration. In some cases, the final wavefront power profile has a center distance configuration. In some cases, the intraocular lens comprises a diffractive shape. In some cases, the first wavefront power profile further comprises a fourth zone disposed peripherally to the third zone, a fourth zone disposed peripherally to the third zone and a fifth zone disposed peripherally to the fourth zone, or a fourth zone disposed peripherally to the third zone, a fifth zone disposed peripherally to the fourth zone, and a sixth zone disposed peripherally to the fifth zone. The total number of zones may be 2, 3, 4, 5, 6, 7, 8, 9 or 10, with respectively k in the range of 1-2, 1-3, 1-4, 1-5, 1-6, 1-7, 1-8, 1-9 or 1-10, without limitation. There may be a cosine-based transformation of sagittal power from each zone to its adjacent zone, or from every other adjacent zone, with zones in-between following the base power profile. For example, in the case of having 3 zones, the first and third zones will generally follow the base power profile, and the transition into and out of the second zone from/to the first and third zones will follow a cosine-based transformation of sagittal power up to and down from a peak value. The above profile [1] further enables improved optical performance in low-light or night viewing conditions by avoiding or reducing side effects, including visual artifacts such as glare and halo, as well as best focus shifts and contrast sensitivity loss. This is achieved by having optical powers that vary as a cosine function of the radial position inside zones of the wavefront to provide smooth phase transitions.

According to some embodiments, zone k is defined by a starting sagittal power ($S_k$), a final sagittal power, a starting radial position ($rz_{ik}$), and a final radial position of the zone ($rz_{ek}$). In some cases, the starting radial position ($rz_{ik}$) of the first zone is zero. In some cases, the final wavefront profile has a relative sagittal power value of zero at least at one radial position and a relative sagittal power value that is positive with a value between 0.1 and 5D for at least at one radial position. In some cases, the final wavefront profile has a relative sagittal power value that is negative (with a value between −0.05 and −2D) at least at one radial position and a relative sagittal power value that is positive (with a value between 0.1 and 5D) for at least at one radial position. In some cases, the sagittal power of the first zone is positive with at least one additional zone with zero or negative relative sagittal power. In some cases, the sagittal power of the first zone is zero or negative with at least one additional zone with positive relative sagittal power. In some cases, the optical power P(r) profile is combined with a spherical intraocular lens design. In some cases, the optical power P(r) profile is combined with an aspheric intraocular lens design corresponding to the first wavefront power profile (base power profile). In some cases, the optical power P(r) profile is combined with an astigmatism-correcting intraocular lens design. In some cases, the optical power P(r) profile is combined with a diffractive profile.

In still another aspect, embodiments of the present invention encompass systems and methods for generating a wavefront power profile for use in the manufacture of an intraocular lens. Exemplary methods can include obtaining a first wavefront power profile corresponding to a theoretical lens, and adding to the first wavefront profile a second wavefront profile defined for one or more zones and delineated by a cosine function, thereby obtaining the final wavefront power profile.

In yet another aspect, embodiments of the present invention encompass systems and methods for fabricating an intraocular lens. Exemplary methods can include obtaining a wavefront power profile, and determining a refractive profile based on the wavefront power profile. The step of determining the refractive profile can include processing the wavefront power profile with an analytical transformation to obtain the refractive profile, as outlined above.

For a fuller understanding of the nature and advantages of the present invention, reference should be made to the ensuing detailed description taken in conjunction with the accompanying drawings.

DETAILED DESCRIPTION OF THE INVENTION

Embodiments of lenses herein disclosed can be configured for placement in the eye of a patient and aligned with the cornea to augment and/or partially replace the function of the crystalline lens. In some embodiments, corrective optics may be provided by phakic IOLs, which can be used to treat patients while leaving the natural lens in place. Phakic IOLs may be angle supported, iris supported, or sulcus supported. IOLs can be further secured with support members that attach the IOL to the eye, e.g., with physical extensions from the IOL into adjacent corneal or iris tissue. Phakic IOLs can also be placed over the natural crystalline lens or piggy-backed over another IOL. Exemplary ophthalmic lenses include contact lenses, phakic lenses, pseudophakic lenses, corneal inlays, and the like. It is also envisioned that the lens shapes disclosed herein may be applied to inlays, onlays, accommodating IOLs, spectacles, and even laser vision correction.

Optical power is related to the second derivative or curvature of an optical shape. In currently available refractive multifocal IOL designs, where different regions of a lens surface have different curvatures, the annular zones may tend to meet at abrupt changes in curvature. An abrupt optical power step between adjacent zones can cause visual artifacts including glare, halos, and decreased contrast sensitivity. Although the effects of zone boundaries can be reduced by inserting matching transition zones, such transition zones can also introduce dysphotopsia effects. Embodiments of the present invention solve these and other problems by implementing surfaces that provide wavefronts having optical powers that vary as a cosine function of the radial position inside zones of the wavefront.

In some cases, the optical power may be referred to as the dioptric power, the refractive power, the focusing power, the sagittal power, wavefront vergence, or the convergence power. In some cases, this is referred to as the sagittal power (D) or wavefront vergence (D). Typically, the wavefront curvature gives the dioptric power of the wavefront. The curvature or the power of the wavefront is generally equivalent or related to the second derivative of the wavefront or wavefront shape. The curvature or power can be provided in units of diopters. The vergence or power profile can refer to the first derivative of the wavefront, divided by the radial position. Embodiments of the present invention encompass lenses that produce emerging or refracted wavefronts having dioptric power profiles that vary as a cosine function of the radial position of the wavefront. There are many different methods available to measure wavefront and power profiles.

Exemplary Intraocular Lens Shapes

Figure 1A:
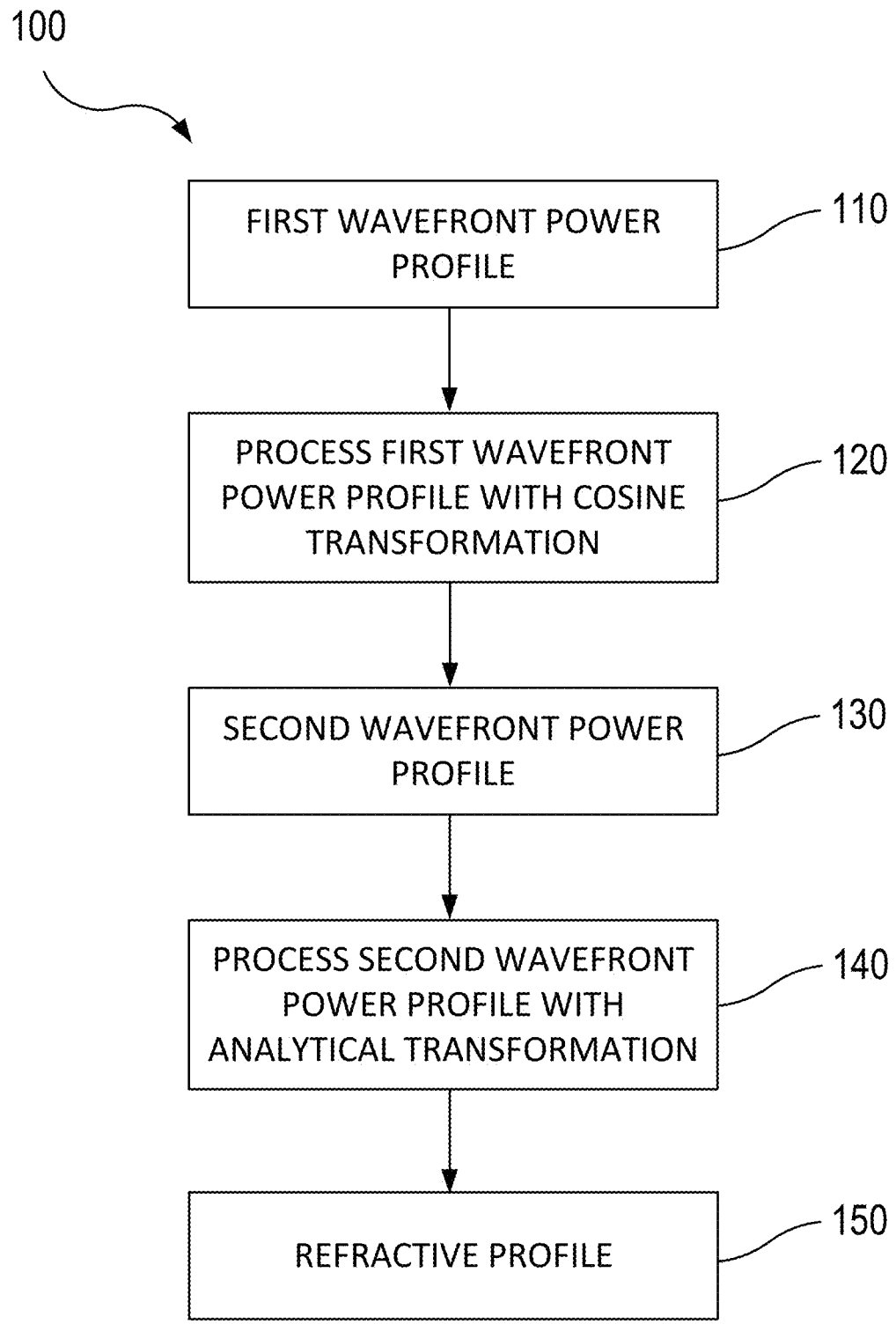
FIG. 1A illustrates aspects of an exemplary method for determining a refractive profile, according to embodiments of the present invention.

Turning now to the drawings, FIG. 1A illustrates aspects of an exemplary method 100 for determining a refractive profile 150, which can be used to fabricate or generate a lens or other refractive treatment element. In some cases, the refractive profile 150 can be used to fabricate an intraocular lens. As shown here, a final wavefront power profile can be obtained by adding to the first wavefront profile a second wavefront profile defined for one or more zones of the wavefront delineated by a cosine function, as indicated by step 120. Also, the final wavefront power profile 130 can be processed with an analytical transformation, as indicated by step 140, to obtain a refractive profile 150 (see above for an example of this transformation). In some embodiments, the refractive profile 150 can be used to fabricate an intraocular lens, such that the intraocular lens has a refractive shape that is based on the refractive profile. In some cases, the refractive profile 150 can be used to generate a vision treatment element or procedure, so as to provide an emerging beam that has a wavefront power profile as described herein. In some cases, the refractive profile can be used in conjunction with a diffractive feature to provide a vision treatment or element as described herein.

With respect to step 120, for example, a cosine transformation can be used to develop a wavefront surface where the optical power $P_k(r)$ varies as a cosine function of the radial position inside zone k, according to the following formula, which may be referred to as Equation 1:

$$P_k(r) = S_k - A_k(-1)^{CosOrderk} * \left[ \frac{-1}{2} + \frac{1}{2}\cos\left[\pi\left[\frac{r^2 - rz_{ik}^2}{rz_{ek}^2 - rz_{ik}^2}\right]\right]^{CosOrderk} \right]$$

In this equation, the amplitude $A_k$ is defined as the difference between the starting and the final sagittal power within zone k. In some embodiments, the amplitude $A_k$ is provided in units of diopters. $S_k$ is the starting sagittal power of zone k. In some embodiments, the starting sagittal power is provided in units of diopters. $S_k$ can be defined as a constant value or as a variable function that depends on the radial coordinate, r, $S_k(r)$. The $rz_{ik}$ and $rz_{ek}$ terms are respectively the starting (initial) and final radial coordinates of zone k. In some embodiments, the starting and final radial coordinates are provided in units of mm. The CosOrderk term can define the power (exponent) of the cosine function of zone k.

As discussed elsewhere herein, the power P(r) across the lens with respect to the radial coordinate, r, is defined by or equates to the power $P_k(r)$ at a given radial coordinate and can correspond to the optical power of the wavefront (or zones of the wavefront) that is emerging from a lens, and the optical power P(r) can be used to determine an optical surface shape or profile using an analytical approach. The power $P_k(r)$ can be added to a radially varying base power profile, B(r), at a given radial coordinate, r, and the constant IOL base power of the lens, $P_{IOL}$, to provide the final power profile of the lens and the paraxial power of the lens:

$$P(r) = P_k(r) + +P_{IOL}.$$

The constant IOL base power of the lens is a constant value (e.g. 20.0 D), the radially varying base power profile, B(r), is a function of radial coordinate r following a polynomial function. B(r) can be zero or it can be a polynomial function designed to induce or correct certain amount of spherical aberration (e.g. to create the power profile of a negative spherical aberration lens or a neutral spherical aberration lens). Together, B(r) and $P_{IOL}$ constitute the base power profile (first wavefront power profile) of the lens.

In exemplary embodiments, the optical power P(r) can correspond to the final wavefront power profile 130 depicted in FIG. 1A. In this way, it is possible to provide a wavefront power profile 130 that is smooth, and the final wavefront power profile can then be converted to a surface shape. Often, the solution will provide only one surface. This approach is different from known fitting or optimization techniques. Known fitting techniques may provide unwanted results or may involve uncontrollable processes, and may result in a non-smooth power profile.

Some embodiments may involve designing a desired power profile, defining a corresponding wavefront, and then extracting (e.g. no fitting) or calculating data or information (e.g. regarding sag) for developing the surface of a lens from the curvature of the wavefront.

Figure 1B:
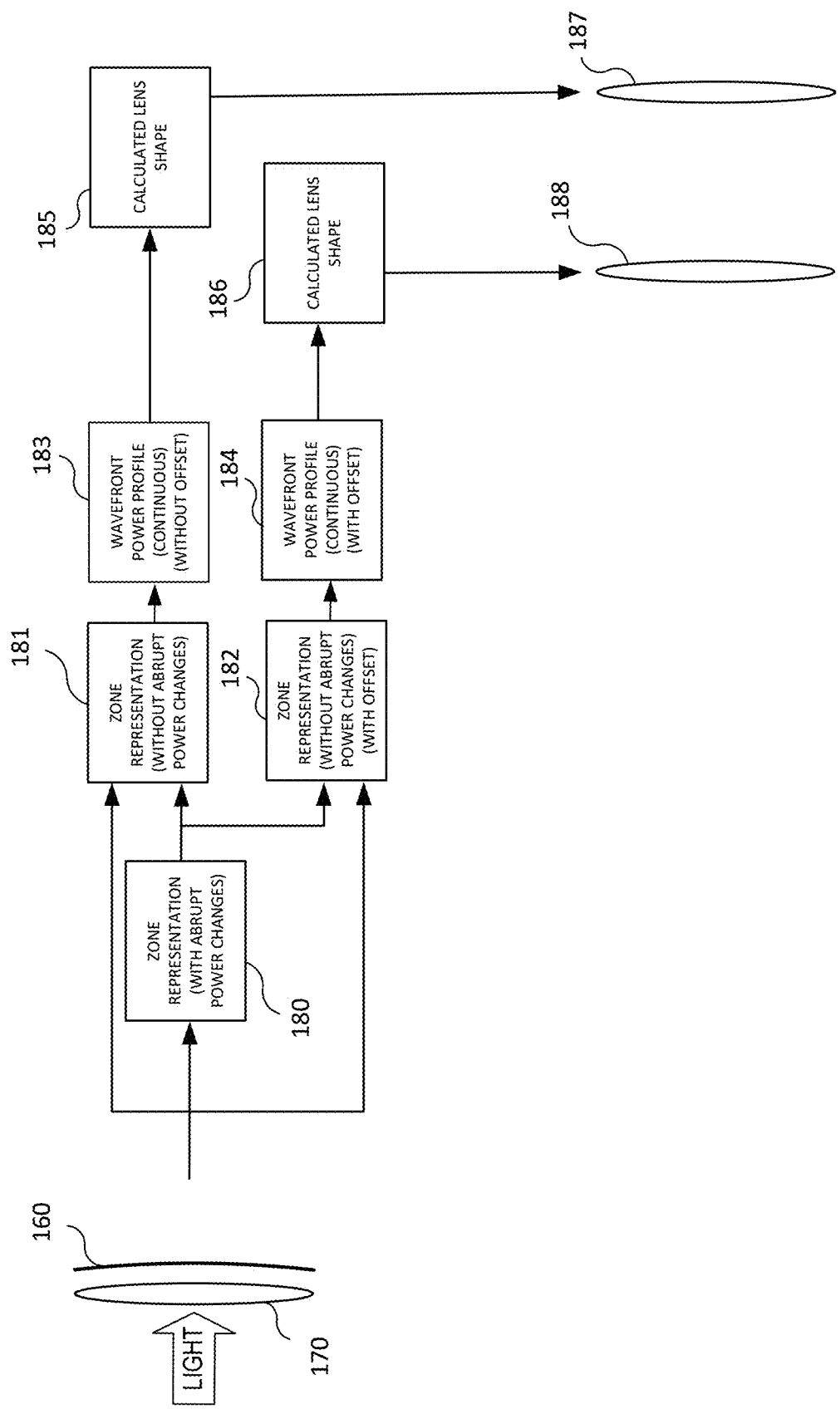
FIG. 1B illustrates aspects of an exemplary method for fabricating or manufacturing a lens or other refractive treatment element, according to embodiments of the present invention.
Figure 2A:
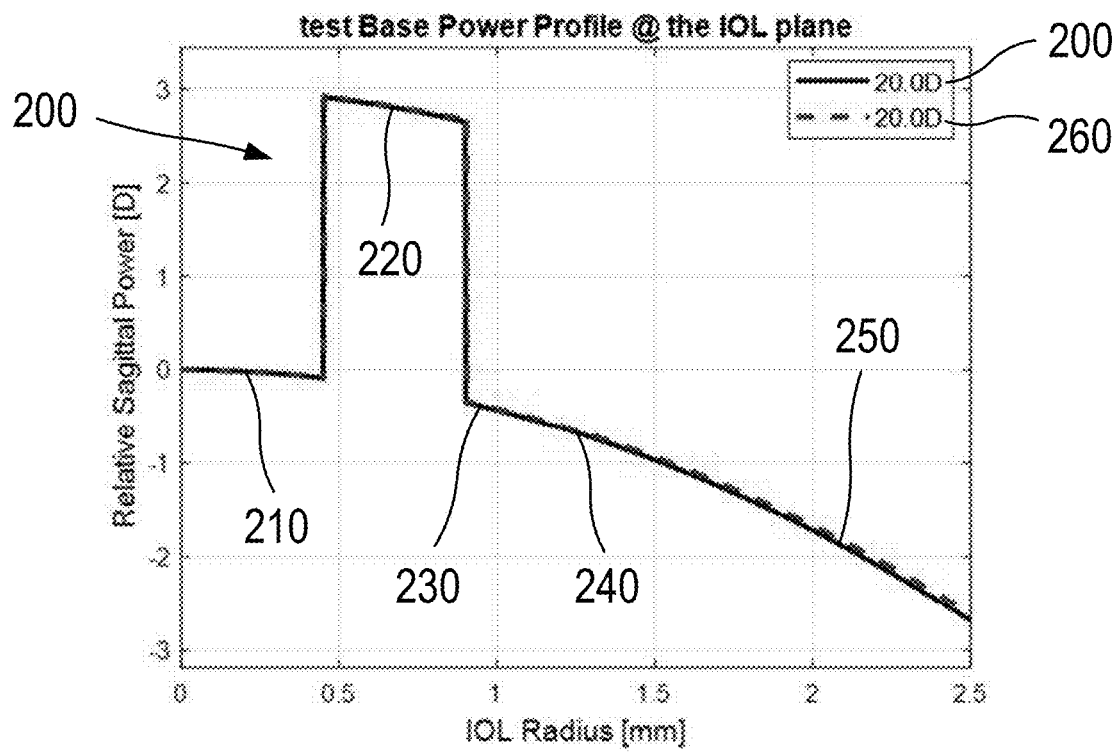
FIG. 2A depicts aspects of a wavefront power profile, according to embodiments of the present invention.

FIG. 1B depicts additional aspects of a method for fabricating or manufacturing a lens (e.g., 187, 188) or other refractive treatment element, according to embodiments of the present invention. As shown here, an initial step involves obtaining a power profile of a wavefront 160 emerging from a hypothetical or theoretical lens 170. The emerging wavefront 160 may have a relative sagittal power profile similar to that which is shown in FIG. 2A. The emerging wavefront power profile may be discontinuous. In some cases, methods may involve identifying zones of the wavefront power profile. Individual zones may have initial/final add powers and radial sizes, for example such as those zones depicted in Table 1. Exemplary embodiments involve determining a refractive shape or refractive profile without using a wavefront representation such as that which is shown in Table 1 (or step 180 or FIG. 2A).

In some cases, abrupt power changes can be removed from the zone representation 180 of the wavefront power profile. For example, with reference to Table 1, this may involve changing the zone 2 initial add power from 3 to 0, and changing the zone 3 initial add power from 0 to 3. Such an approach may provide a zone representation 181 such as that which is depicted in Table 2 (see also FIG. 3A). In some cases, a zone representation 181 such as that which is depicted in Table 2 can be provided without having first provided an initial zone representation 180 such as that which is depicted in Table 1. In some cases, abrupt power changes can be removed from the zone representation 180 of the wavefront power profile as describe above, and an offset can be introduced. For example, with reference to Table 1, this may involve changing the zone 1 initial and final add powers from 0 to −0.25, changing the zone 2 initial add power to −0.25, changing the zone 3 final add power to −0.25, and changing the zone 4 initial add power to −0.25. Such an approach may provide a zone representation 182 such as that which is depicted in Table 3 (see also FIG. 4A). In some cases, a zone representation 182 such as that which is depicted in Table 3 can be provided without having first provided an initial zone representation 180 such as that which is depicted in Table 1.

Figure 3A:
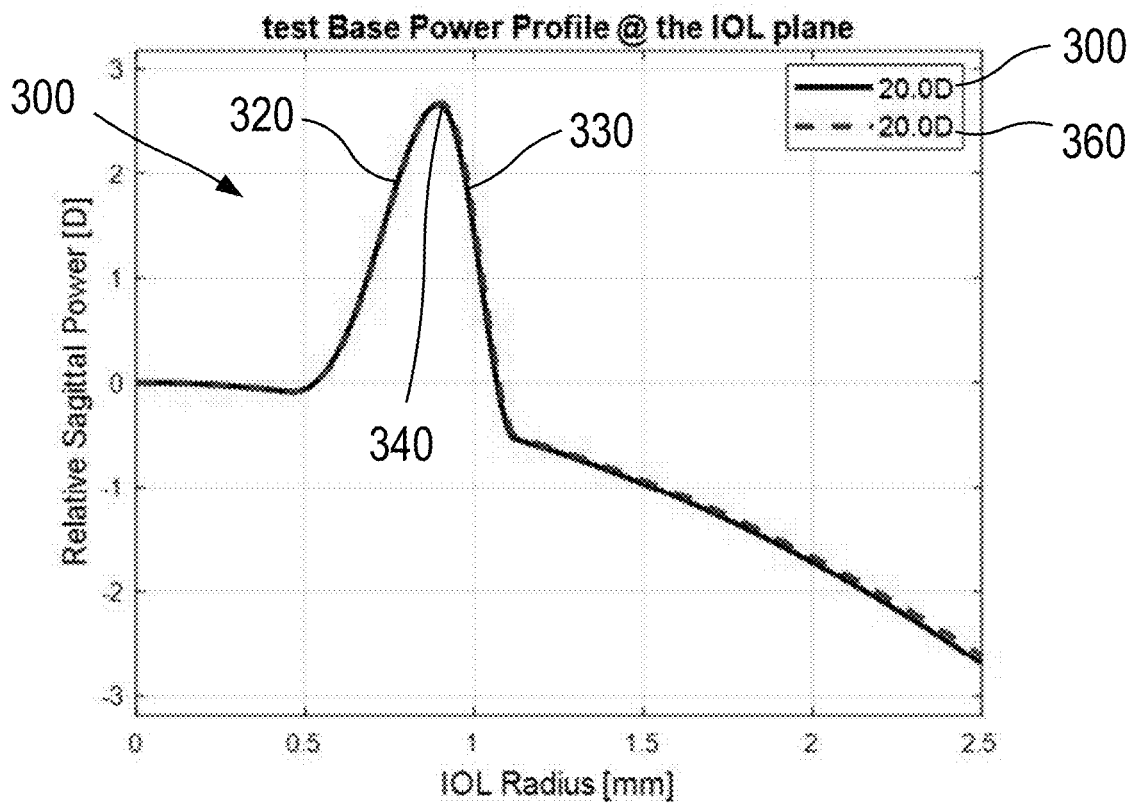
FIG. 3A depicts aspects of a wavefront power profile, according to embodiments of the present invention.
Figure 4A:
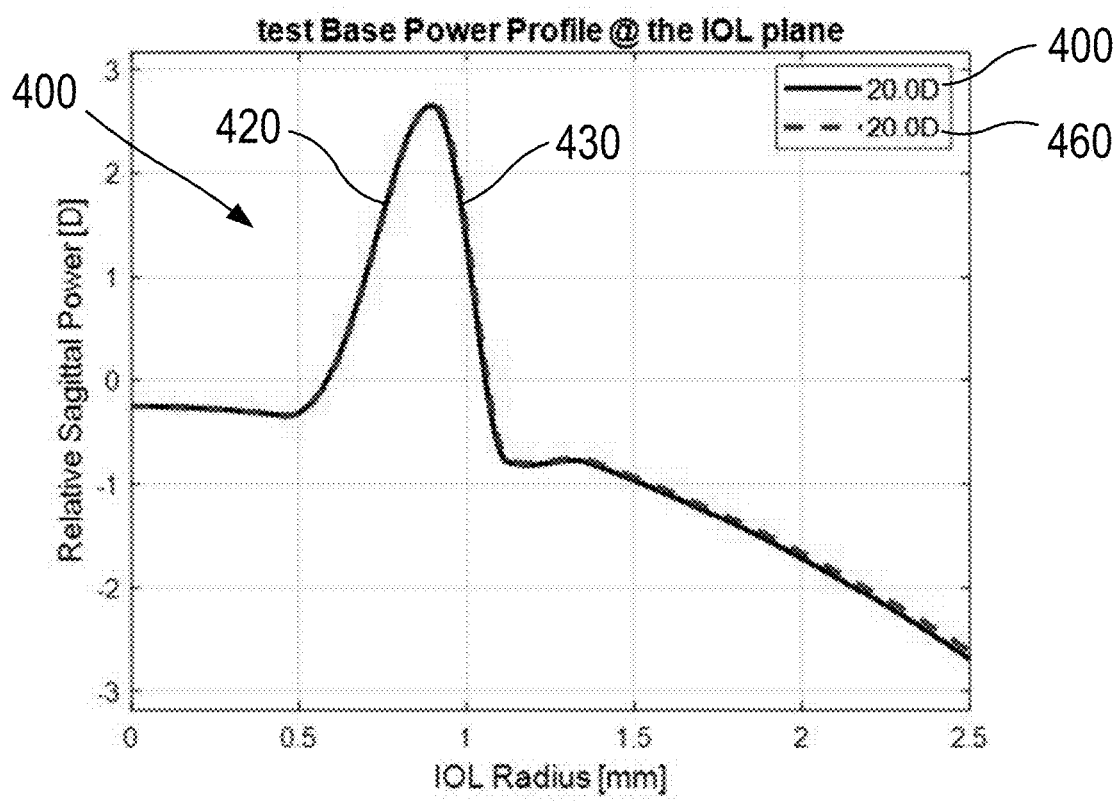
FIG. 4A depicts aspects of a wavefront power profile, according to embodiments of the present invention.

Based on zone representation 181, it is possible generate a wavefront power profile 183. In some cases, this may involve using a cosine equation (e.g. Equation 1) to generate a continuous power profile, while maintaining initial/final add powers and zone radial sizes. Such a wavefront power profile is depicted in FIG. 3A. Relatedly, based on zone representation 182, it is possible to generate a wavefront power profile 184. In some cases, this may involve using a cosine equation (e.g. Equation 1) to generate a continuous power profile, while maintaining initial/final add powers and zone radial sizes. Such a wavefront power profile is depicted in FIG. 4A.

Based on wavefront power profile 183, it is possible to calculate a lens shape or refractive profile 185. Such a lens surface shape, applied to a spherical base curvature or surface, is characterized in FIG. 3B. Relatedly, such a lens surface shape can be applied to any base surface, including for example, an aspheric surface of the TECNIS® Monofocal 1-Piece IOL (Model ZCB00). In some cases, this process may involve using an analytical solution as outlined above. Relatedly, based on wavefront power profile 184, it is possible to calculate a lens shape or refractive profile 186. Such a lens surface shape, applied to a spherical base curvature, is characterized in FIG. 4B. In some cases, this process may involve using an analytical solution as outlined above. Based on calculated lens shape 185, it is possible to fabricate a lens 187. Relatedly, based on calculated lens shape 186, it is possible to fabricate a lens 188.

Table 1 below provides parameters for an exemplary wavefront power profile, according to embodiments of the present invention, as will be described below with reference to FIGS. 2A-2C. In an intraocular lens embodiment, Zone 1 can be disposed centrally on the lens, and Zones 2 to 5 can be disposed peripherally to Zone 1, in their respective order. In some cases, the wavefront power profile is discontinuous, without offsets.

TABLE 1

|  | Zone 1 | Zone 2 | Zone 3 | Zone 4 | Zone 5 |
| --- | --- | --- | --- | --- | --- |
| K | 1 | 2 | 3 | 4 | 5 |
| S (±0.25 D) | 0 | 3 | 0 | 0 | 0 |
| A (±0.25 D) | 0 | 0 | 0 | 0 | 0 |
| CosOrder | 1 | 1 | 1 | 1 | 1 |
| $rz_i$ (±0.1 mm) | 0.0 | 0.5 | 0.9 | 1.1 | 1.4 |
| $rz_e$ (±0.1 mm) | 0.5 | 0.9 | 1.1 | 1.4 | 2.5 |

In some embodiments, radial sizes can be calculated to provide an area to each defined zone that results in the desired balance for the through focus performance.

FIG. 2A depicts a wavefront power profile corresponding to the parameters provided in Table 1 added to the base (first) power profile of a standard negative spherical aberration lens. As shown in FIG. 2A, the power profile 200 contains abrupt changes in power, or abrupt changes in curvature (e.g. at radial distances 0.45 mm and 0.90 mm). In some embodiments, power profile 200 can be referred to as a theoretical or hypothetical power profile. Zone 1, here labeled 210, provides distance focus, and Zone 2, here labeled 220, provides near focus. Zone 3, here labeled 230, Zone 4, here labeled 240, and Zone 5, here labeled 250, provide distance focus. As shown here, Zone 2 provides an add power of 3 diopters. In some cases, the add power can be defined as the relative power with respect to the constant IOL base power of the lens (e.g. base power of 20 diopters). The power profile 200 does not include transition zones between the near and distance zones, as the power changes abruptly when going from the central Zone 1 (distance focus) to the peripheral Zone 2 (near focus), and when going from the peripheral Zone 2 (near focus) to the peripheral Zone 3 (distance focus).

Figure 2B:
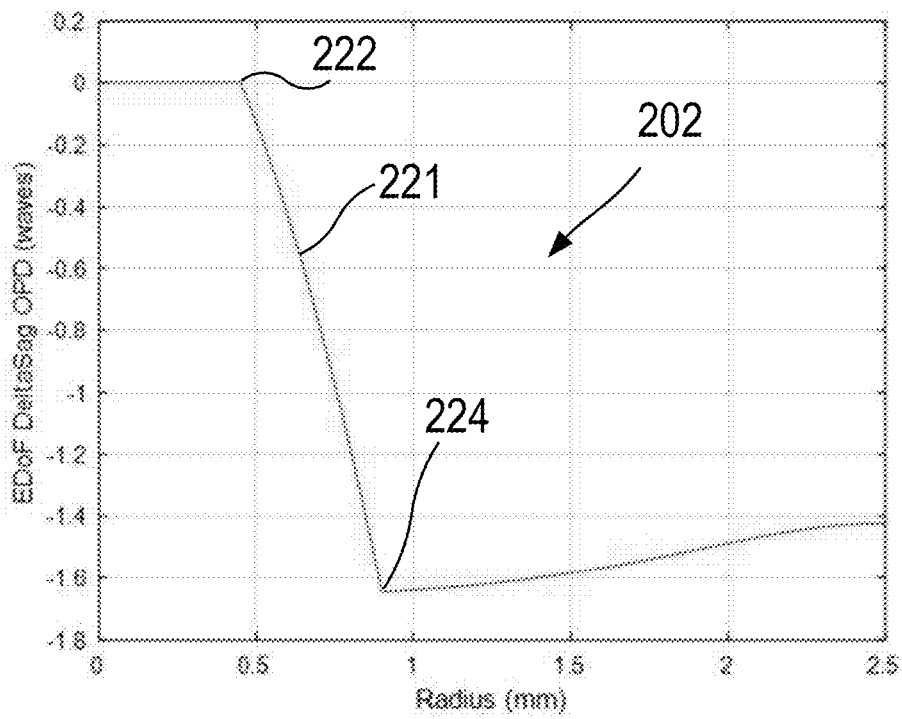
FIG. 2B depicts aspects of a refractive profile, according to embodiments of the present invention.

FIG. 2B depicts aspects of a refractive profile corresponding to Table 1. The Extended Depth of Focus (EDoF) DeltaSag Optical Path Difference (OPD) depicted here corresponds to the surface shape of a lens, where the base curvature has been removed. In some cases, the base curvature is spherical. In some cases, the base curvature is aspherical. The EDoF DeltaSag OPD can refer to the amount of curvature or sag that is added to a base curvature. In some cases, this profile 202 shows how the lens surface can deviate from a base curvature, which may be a monofocal lens profile. As shown here, the profile 202 can correspond to a function that is not differentiable, because of the "corners" 222 and 224 at the outer borders of Zone 2, here labeled as 221. Given a refractive lens profile that corresponds to the DeltaSag profile 202 or physical surface of the lens illustrated in FIG. 2B, it is possible to generate a lens power profile using a ray tracing technique. Such a lens power profile 260 is depicted in FIG. 2A. As shown there, the lens power profile 260 closely approximates the theoretical or hypothetical power profile 200.

Figure 2C:
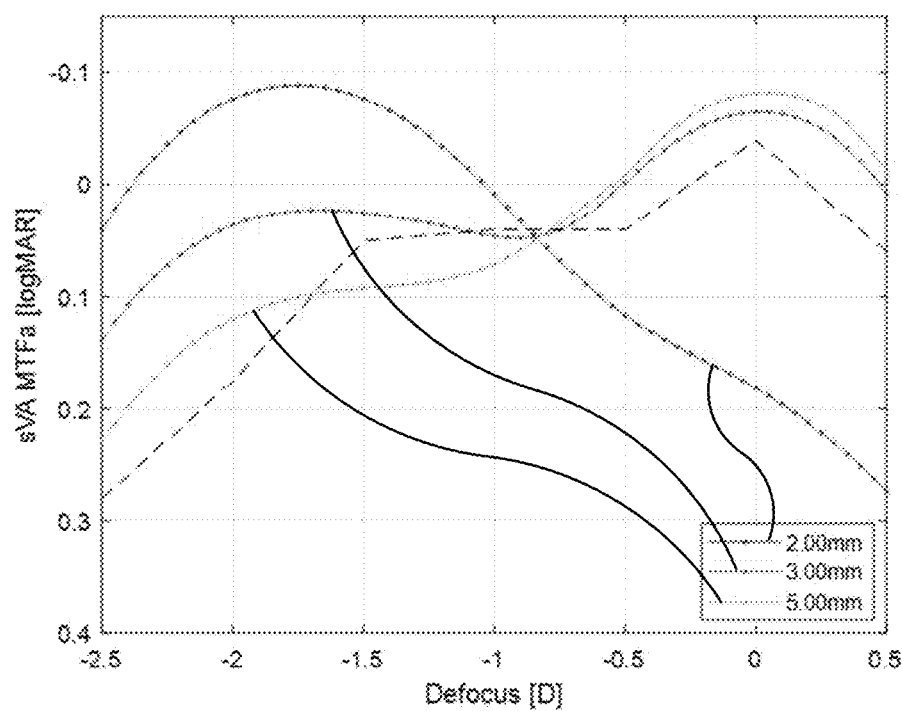
FIG. 2C depicts aspects of through focus Simulated Visual Acuity (sVA) area under the Modulation Transfer Function (MTFa) curves for a lens, according to embodiments of the present invention.

FIG. 2C depicts the through focus Simulated Visual Acuity (sVA) area under the Modulation Transfer Function (MTFa) (see Alarcon et al. *Preclinical metrics to predict through-focus visual acuity for pseudophakic patients*, Biomedical Optics Express 7:1877-1888, 2016) curves for a lens with a power profile corresponding to the parameters provided in Table 1. From the depicted plots it can be seen that the abrupt phase changes introduced by power profile 260 provide significant differences in through focus performance for different pupil sizes, with large best focus shifts for small pupils.

Table 2 below provides parameters for an exemplary wavefront power profile, according to embodiments of the present invention, as will be described below with reference to FIGS. 3A-3C. In an intraocular lens embodiment, Zone 1 can be disposed centrally on the lens, and the Zones 2 to 5 can be disposed peripherally to Zone 1, in their respective order. In some cases, the wavefront power profile is continuous, without offsets.

TABLE 2

|  | Zone 1 | Zone 2 | Zone 3 | Zone 4 | Zone 5 |
| --- | --- | --- | --- | --- | --- |
| k | 1 | 2 | 3 | 4 | 5 |
| S a | 0 | 0 | 3 | 0 | 0 |
| A (±0.25 D) | 0 | −3 | 3 | 0 | 0 |
| CosOrder | 1 | 1 | 1 | 1 | 1 |
| $rz_i$ (±0.1 mm) | 0.0 | 0.5 | 0.9 | 1.1 | 1.4 |
| $rz_e$ (±0.1 mm) | 0.5 | 0.9 | 1.1 | 1.4 | 2.5 |

Relative to Table 1, the Zone 2 initial add power (A) has been changed from 3 diopters to 0 diopters and the Zone 3 initial add power has been changed from 0 diopters to 3 diopters.

FIG. 3A depicts a wavefront power profile 300 corresponding to the parameters provided in Table 2 added to the base (first) power profile of a standard negative spherical aberration lens. As discussed elsewhere herein, a fabrication method can involve designing a power profile in zones (e.g. as shown in Table 2) and then using a cosine equation (e.g. Equation 1) to build a continuous power profile (e.g. profile 300). As shown in FIG. 3A, the power profile 300 does not contain abrupt changes in power or abrupt changes in curvature, such as those shown in FIG. 2A. The above parameters provide improved optical performance in low-light or night viewing conditions by avoiding or reducing side effects, including visual artifacts such as glare and halo, as well as best focus shifts and contrast sensitivity loss. As shown here, the power profile 300 provides an add power of 3 diopters at the interface between Zone 2, here labeled 320, and Zone 3, here labeled 330. In some cases, the add power can be defined as the relative power with respect to the base power of the lens (e.g. base power of 20 diopters). The power profile 300 can include one or more zones having a continuous change in power from distance to near, that provides an Extended Depth of Focus (EDoF) behavior or performance. In some cases, such zones can include instances where the power changes when going from distance focus to near focus (e.g. Zone 2), and when going from near focus to distance focus (e.g. Zone 3). In some cases, such zones can be functional zones that contribute to generate smoother VA curves (EDoF).

Figure 3B:
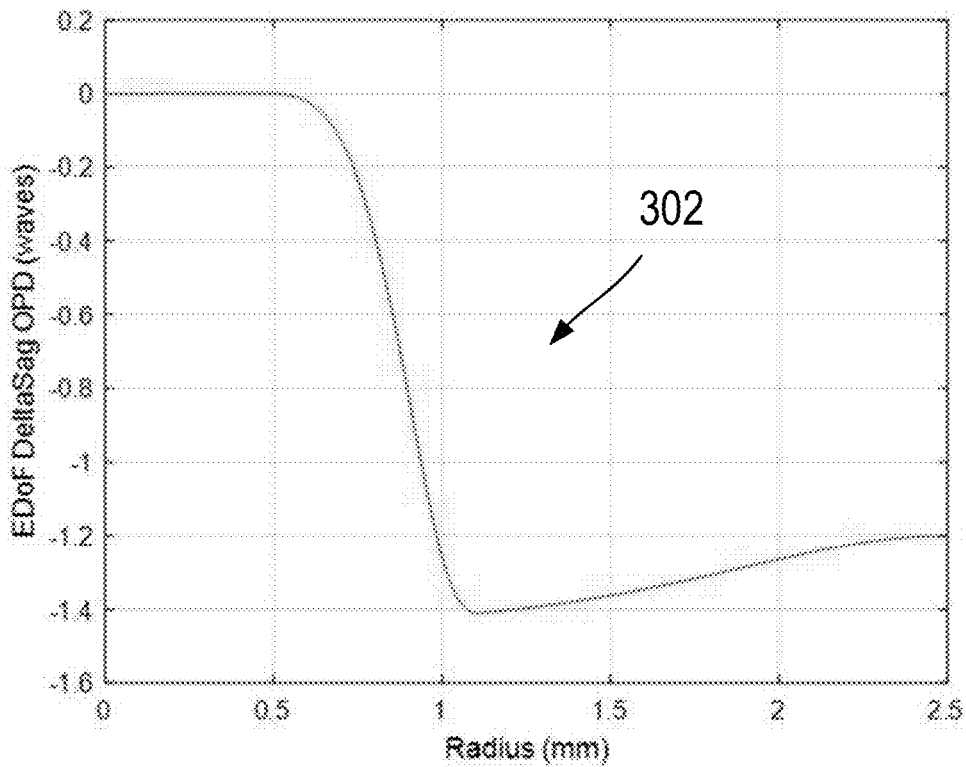
FIG. 3B depicts aspects of a refractive profile, according to embodiments of the present invention.

FIG. 3B depicts aspects of a refractive profile corresponding to Table 2. The Extended Depth of Focus (EDoF) DeltaSag Optical Path Difference (OPD) depicted here corresponds to the surface shape of a lens, where the base curvature has been removed. In some cases, the base curvature is spherical. In some cases, the base curvature is aspherical. The EDoF DeltaSag OPD can refer to the amount of curvature or sag that is added to a base curvature. In some cases, this profile 302 shows how the lens surface can deviate from a base curvature, which may be a monofocal lens profile. In FIG. 3B and in other figures, DeltaSag is provided in optical path difference (OPD) units for the design wavelength (waves). In some cases, the y axis can be changed to metric units (mm).

In some cases, the DeltaSag can be very small relative to the sagitta of the lens. As shown here, the profile 302 can correspond to a function that is differentiable, because there are no "corners" such as those depicted in FIG. 2B. Given a refractive lens profile that corresponds to the DeltaSag profile 302 illustrated in FIG. 3B, it is possible to generate a lens power profile using a ray tracing technique. Such a lens power profile 360 is depicted in FIG. 3A. As shown there, the lens power profile or simulated profile 360 closely approximates the power profile 300.

Given the optical power of the wavefront, it is possible to calculate the sag of the originating surface. First, the power profile $P(r)$, which is the optical power variation expressed in diopters as a function of radial distance from the center to the edge of the lens optic zone, can be calculated and stored. Next, the radial wavefront phase profile $W(r)$ can be calculated by integrating the final power profile using the following expression $W(r)=\int P(r) \cdot r \, dr$. Since the power map can be considered to have rotational symmetry, the resultant wavefront phase profile can be spun around the origin of the radial coordinates to obtain the wavefront phase map, which will be also rotationally symmetric. In some cases, the terms "wavefront phase profile" and "wavefront phase map" can be related to the term "wavefront power profile" as depicted in FIG. 3A. In some cases, the phase profile is the wavefront profile (in units of the wavelength used) converted to radians. It can be obtained by multiplying the wave profile by the have number k, where $k=2\pi/\text{wavelength}$. In some cases, the wavefront map is a 2 D representation of the wavefront profile (1 D).

This methodology can be modified to obtain non-rotational symmetric wavefront phase maps using the following expression $W(\alpha)=\sin^2 \alpha \cdot P_S(r)+\cos^2 \alpha \cdot P_T(r)$, where $P_S(r)$ and $P_T(r)$ are the radial power profiles for the maximum (tangential) and minimum (sagittal) power meridians of the eye, respectively, and a is a value from 0 to 360 degrees.

The power profile 300 shown in FIG. 3A can be constructed using a cosine formula described elsewhere herein. Advantageously, the cosine transformation approach can provide improved outcomes relative to other approaches which may involve the use of parabolic equations, polynomial equations, and the like. In some cases, an advantage of the cosine transformation is the resulting continuous surface. Cosine based embodiments disclosed herein can provide for smoother transitions in curvature, better performance with regard to halo, and less dependence on pupil size and decentration. For example, cosine based embodiments can provide for improved performance when the wearer's pupil changes from one size or diameter to another. In some cases, this may not be related to the cosine transformation of the power profile, and without being bound by any particular theory, it is believed it can be related to the offsets introduced in the power profile. In some cases, the cosine approach can provide power profiles where the interface between adjacent zones is associated with the same power value, where connections between adjacent zones are smooth, and where connections between adjacent zones are tangential.

What is more, defining the wavefront power profile 300 or sagittal optical power (e.g. where wavefront profile can refer to a radial cut of the wavefront) to vary as a cosine function of the radial position can create an extension of the depth of focus without discrete focusing positions, which results in a smoother through focus behavior. In some cases, the through focus behavior comes from the power change along the profile. In some cases, the cosine transformation can make it smoother. In addition, adjacent zones can meet at points with the same curvature avoiding abrupt changes in the second derivative of the surface. This method also allows for a complete control of the final design by avoiding the need to fit the surface with a high order polynomial.

According to some embodiments, the height of the add power peak 340 or zone can have a significant impact on the performance of the manufactured lens. As shown in FIG. 3A, the add power (or relative sagittal power) associated with the peak can have a maximum or upper value of about 3 diopters. In some cases, this value can be higher than 3 diopters. The value may depend on the through focus range that is desired. In some cases, the add power (or relative sagittal power) associated with the peak can have a minimum or lower value of about 1 diopter. As discussed elsewhere herein, individual zones associated with the wavefront power profile 300 can have value ranges for their initial or starting points and for their final or ending points. See, for example, Table 4 and Table 5.

As discussed elsewhere herein, a fabrication method can involve obtaining the wavefront power profile (e.g. profile 300 of FIG. 3A) and then calculating a surface or refractive profile that provides such a wavefront power profile. The surface can be calculated using, for example, a DeltaSag profile 302 or a sagitta corresponding to the profile 302. In some cases, P can be the total power profile. When the EDoF is placed in the posterior surface, the input parameter can be P1 which is the power of only the first surface. P2 can be obtained to calculate the second surface. P2 can be based on the difference between P and P1. The OPD can be based on the radius. The SagPosterior can be based on the OPD. To place the EDoF in the anterior sag the input can be P2 and it is possible to calculate P1 by reversing the relationship.

Embodiments of the present invention encompass techniques for obtaining sag information or values from a power profile. In some cases, such power profiles may be provided as smooth power profiles, such as those depicted in FIGS. 3A, 4A, 5A, 8A, and 9A, and the resulting sag information or values can be provided as EDoF DeltaSag OPD profiles (or other corresponding shape representations) such as those depicted in FIGS. 3B, 4B, 5A, 8A, and 9A. Analytical techniques can be used to obtain such sag information or values from the power profiles, as outline above. In some cases, the analytical techniques do not use optimization.

Figure 3C:
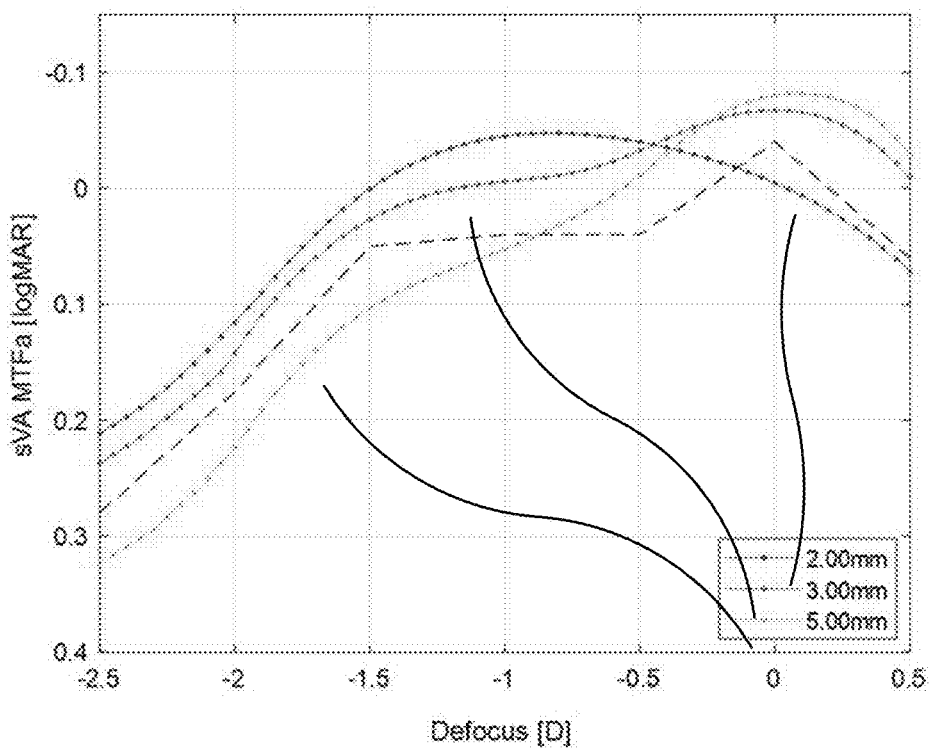
FIG. 3C depicts aspects of through focus Simulated Visual Acuity (sVA) area under the Modulation Transfer Function (MTFa) curves for a lens, according to embodiments of the present invention.

FIG. 3C depicts Simulated Visual Acuity (sVA) calculated from the area under the Modulation Transfer Function (MTFa) curves (see Alarcon et al. *Preclinical metrics to predict through-focus visual acuity for pseudophakic patients*, Biomedical Optics Express 7:1877-1888, 2016) for different pupil sizes, corresponding to the parameters provided in Table 2. Compared to profile 260, profile 360 shows significantly lower pupil dependency, especially for lower pupil diameters, along with a monotonical decrease in simulated visual acuity provided by the smoother power transition.

Figure 3D:
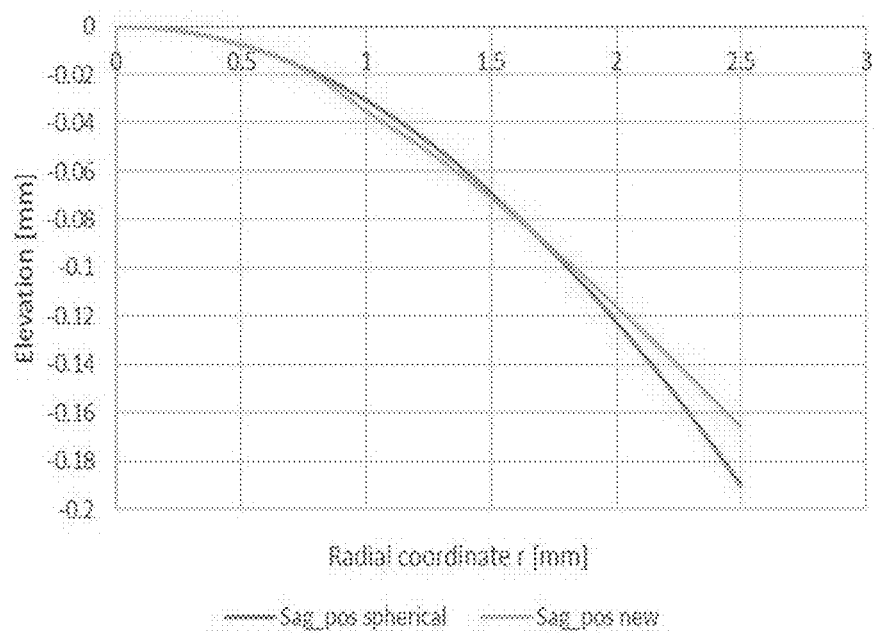
FIG. 3D depicts a difference in shape between the original posterior surface of the intraocular lens and the new shape of the posterior surface resulting from the power profile depicted in FIG. 3A, by way of one example.

FIG. 3D depicts the difference in shape between the original posterior surface of the intraocular lens and the new shape of the posterior surface that would result in the power profile described in FIG. 3A, corresponding to the analytical transformation described above.

Table 3 below provides parameters for an exemplary wavefront power profile, according to embodiments of the present invention, as will be described below with reference to FIGS. 4A-4C. In an intraocular lens embodiment, Zone 1 can be disposed centrally on the lens, and the Zones 2 to 5 can be disposed peripherally to Zone 1, in their respective order. In some cases, the wavefront power profile is continuous, with offsets (e.g. Zone 1 initial and final add powers at −0.25 diopters).

TABLE 3

|  | Zone 1 | Zone 2 | Zone 3 | Zone 4 | Zone 5 |
|---|---|---|---|---|---|
| k | 1 | 2 | 3 | 4 | 5 |
| S (±0.25 D) | −0.25 | −0.25 | 3 | −0.25 | 0 |
| A (±0.25 D) | 0 | −3.25 | 3.25 | −0.25 | 0 |
| CosOrder | 1 | 1 | 1 | 1 | 1 |
| $rz_i$ (mm) | 0.00 | 0.5 | 0.9 | 1.1 | 1.4 |
| $rz_e$ (mm) | 0.5 | 0.9 | 1.1 | 1.4 | 2.50 |

Relative to Table 1, the Zone 1 initial add power has been changed from 0 diopters to −0.25 diopters, the Zone 1 final add power has been changed from 0 diopters to −0.25 diopters, the Zone 2 initial add power has been changed from 3 diopters to −0.25 diopters, the Zone 3 initial add power has been changed from 0 diopters to 3 diopters, the Zone 3 final add power has been changed from 0 diopters to −0.25 diopters, and the Zone 4 initial add power has been changed from 0 diopters to −0.25 diopters.

FIG. 4A depicts a wavefront power profile corresponding to the parameters provided in Table 3 added to the base (first) power profile of a standard negative spherical aberration lens. As shown in FIG. 4A, the power profile 400 does not contain abrupt changes in power or abrupt changes in curvature, such as those shown in FIG. 2A. The above parameters provide improved optical performance in low-light or night viewing conditions by avoiding or reducing side effects, including visual artifacts such as glare and halo, as well as best focus shifts and contrast sensitivity loss. As shown here, the power profile 400 provides an add power of 3 diopters at the interface between Zone 2, here labeled 420, and Zone 3, here labeled 430. In some cases, the add power can be defined as the relative power with respect to the base power of the lens (e.g. base power of 20 diopters). The power profile 400 can include one or more zones having a continuous change in power from distance to near, that provides an Extended Depth of Focus (EDoF) behavior or performance. In some cases, such zones can include instances where the power changes when going from distance focus to near focus (e.g. Zone 2), and when going from near focus to distance focus (e.g. Zone 3). In some cases, such zones can be functional zones that contribute to generate smoother VA curves (EDoF).

Figure 4B:
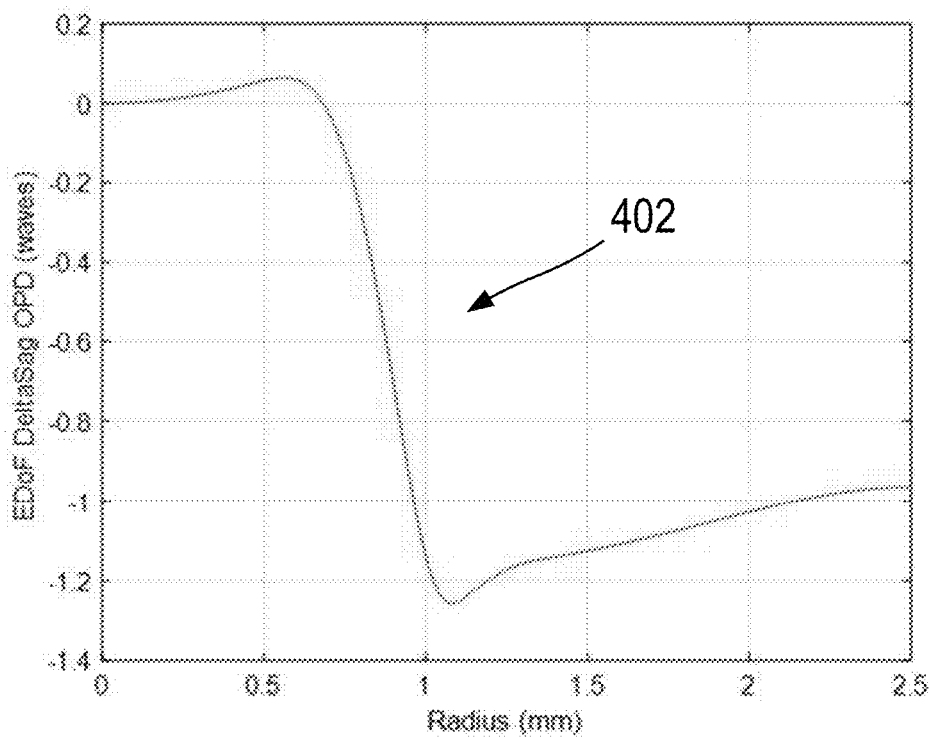
FIG. 4B depicts aspects of a refractive profile, according to embodiments of the present invention.

FIG. 4B depicts aspects of a refractive profile corresponding to Table 3. The Extended Depth of Focus (EDoF) DeltaSag Optical Path Difference (OPD) depicted here corresponds to the surface shape of a lens, where the base curvature has been removed. In some cases, the base curvature is spherical. In some cases, the base curvature is aspherical. The EDoF DeltaSag OPD can refer to the amount of curvature or sag that is added to a base curvature. In some cases, this profile 402 shows how the lens surface can deviate from a base curvature, which may be a monofocal lens profile. As shown here, the profile 402 can correspond to a function that is differentiable, because there are no "corners" such as those depicted in FIG. 2B. Given a refractive lens profile that corresponds to the DeltaSag profile 402 illustrated in FIG. 4B, it is possible to generate a lens power profile using a ray tracing technique. Such a lens power profile 460 is depicted in FIG. 4A. As shown there, the lens power profile 460 closely approximates the power profile 400.

Figure 4C:
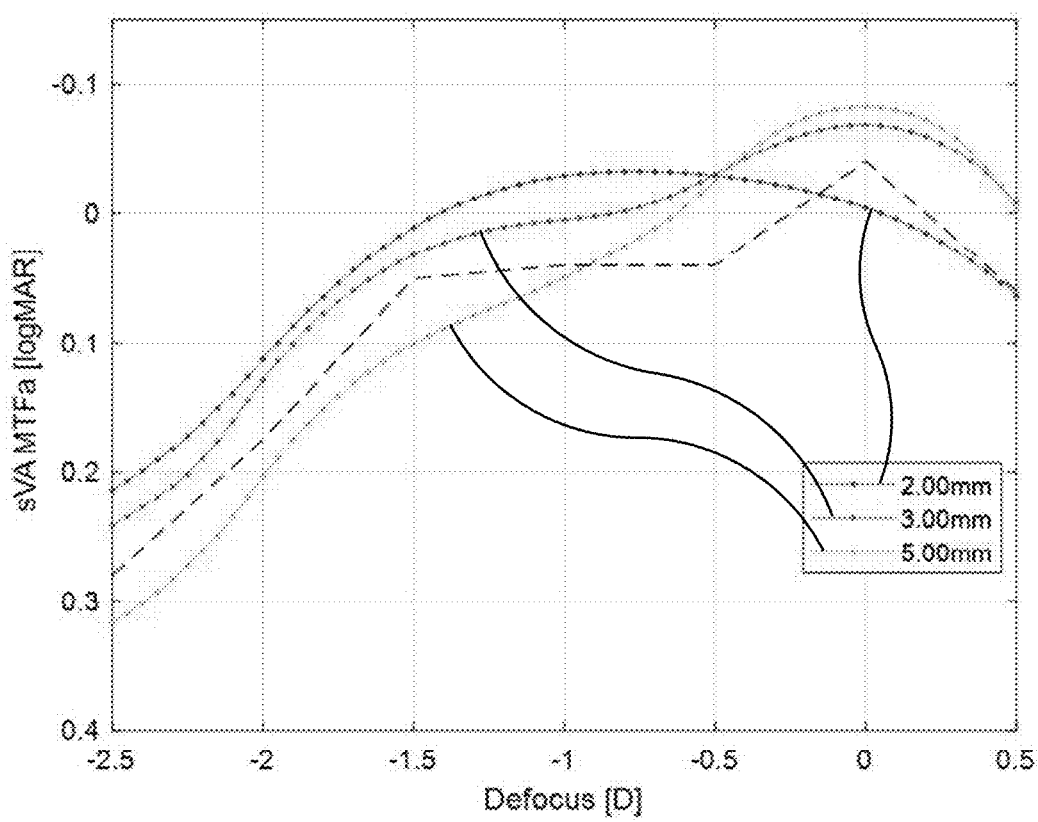
FIG. 4C depicts aspects of through focus Simulated Visual Acuity (sVA) area under the Modulation Transfer Function (MTFa) curves for a lens, according to embodiments of the present invention.

FIG. 4C depicts Simulated Visual Acuity (sVA) calculated from the area under the Modulation Transfer Function (MTFa) curves (see Alarcon et al. *Preclinical metrics to predict through-focus visual acuity for pseudophakic patients*, Biomedical Optics Express 7:1877-1888, 2016) for different pupil sizes corresponding to the parameters provided in Table 3. Compared to profile 360, profile 460 shows an improvement in pupil dependency for 2 mm and 3 mm pupil diameters, provided by the negative phase offsets (or negative power offsets) here introduced.

According to some embodiments, it is possible to adjust the power and/or size of the zones, for example to increase the depth of focus. Table 3A below provides parameters for an exemplary wavefront power profile, according to embodiments of the present invention, as will be described below with reference to FIGS. 4D-4F.

TABLE 3A

|  | Zone 1 | Zone 2 | Zone 3 | Zone 4 | Zone 5 |
|---|---|---|---|---|---|
| k | 1 | 2 | 3 | 4 | 5 |
| S (±0.25 D) | −0.25 | −0.25 | 4 | −0.20 | 0 |
| A (±0.25 D) | 0 | −4.25 | 4.20 | −0.20 | 0 |
| CosOrder | 1 | 1 | 1 | 1 | 1 |
| $rz_i$ (±0.1 mm) | 0.00 | 0.5 | 0.9 | 1.1 | 1.5 |
| $rz_e$ (±0.1 mm) | 0.5 | 0.9 | 1.1 | 1.5 | 2.50 |

Figure 4D:
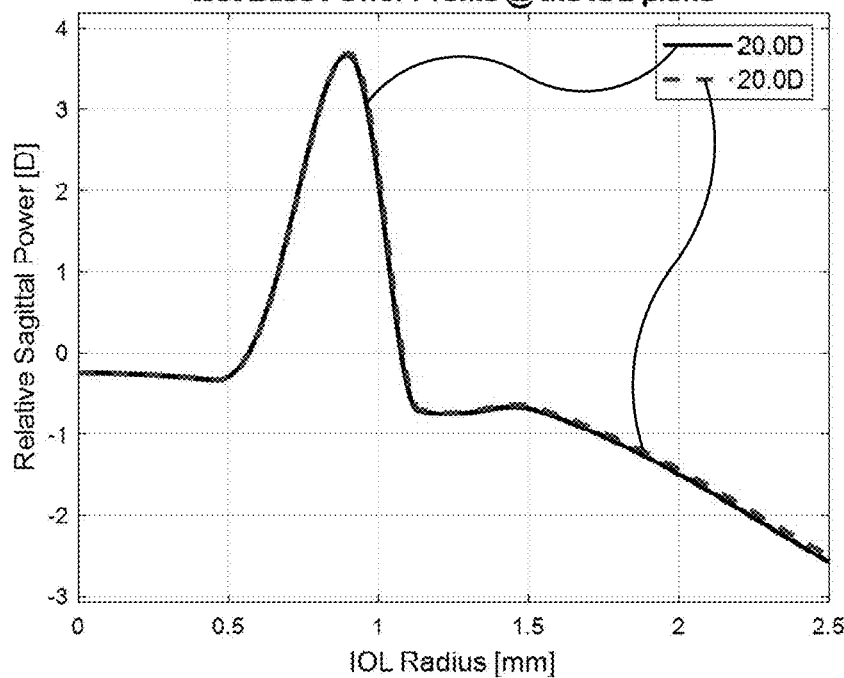
FIG. 4D depicts aspects of a wavefront power profile, according to embodiments of the present invention.
Figure 4E:
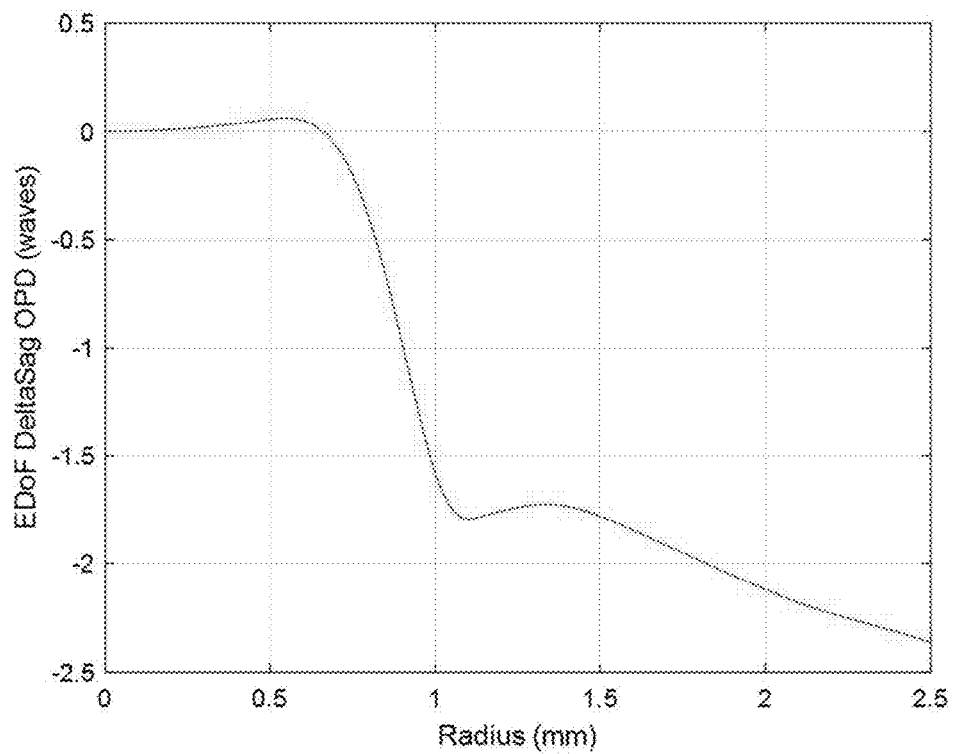
FIG. 4E depicts aspects of a refractive profile, according to embodiments of the present invention.
Figure 4F:
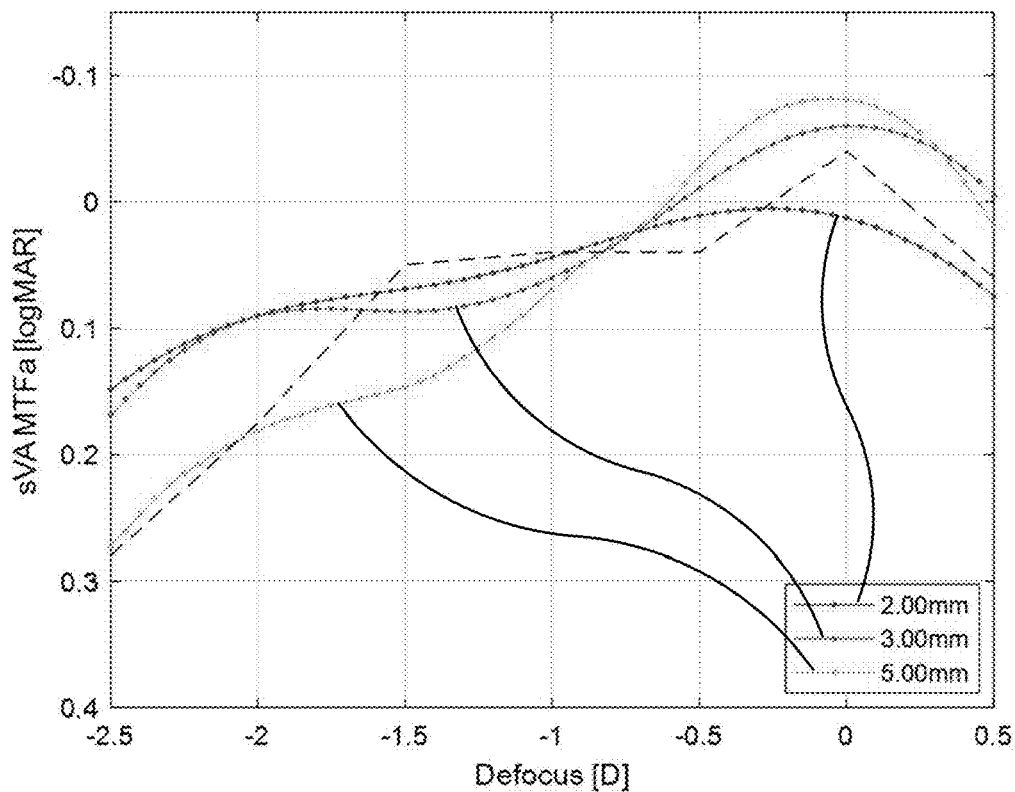
FIG. 4F depicts aspects of through focus Simulated Visual Acuity (sVA) area under the Modulation Transfer Function (MTFa) curves for a lens, according to embodiments of the present invention.

FIGS. 4D, 4E, and 4F correspond to Table 3A. In some cases, the relationship between FIGS. 4D, 4E, and 4F to Table 3A is similar to the relationship between FIGS. 2A, 2B, and 2C to Table 1, the relationship between FIGS. 3A, 3B, and 3C to Table 2, the relationship between FIGS. 4A, 4B, and 4C to Table 3, and/or the relationship between FIGS. 5A, 5B, and 5C to Table 4. When comparing FIGS. 4C and 4F, it can be noticed that increasing the added power increases the range of vision and improves near performance.

Table 4 below provides parameters for an exemplary wavefront power profile, according to embodiments of the present invention, as will be described below with reference to FIGS. 5A-5C. In some cases, the wavefront power profile is particularly well suited for use with small pupils. As further discussed below, a central zone can be added (e.g. for near focus) to create an even more pupil dependent design with better performance for small pupils.

TABLE 4

|  | Zone 1 | Zone 2 | Zone 3 | Zone 4 | Zone 5 | Zone 6 |
|---|---|---|---|---|---|---|
| k | 1 | 2 | 3 | 4 | 5 | 6 |
| S (±0.25 D) | 2.25 | 2.25 | −0.25 | −0.25 | 2.25 | 0 |
| A (±0.25 D) | 0 | 2.50 | 0 | −2.50 | 2.25 | 0 |

TABLE 4-continued

|  | Zone 1 | Zone 2 | Zone 3 | Zone 4 | Zone 5 | Zone 6 |
|---|---|---|---|---|---|---|
| CosOrder | 1 | 1 | 1 | 1 | 1 | 1 |
| $rz_i$ (±0.1 mm) | 0.00 | 0.4 | 0.7 | 1.1 | 1.3 | 1.5 |
| $rz_e$ (±0.1 mm) | 0.4 | 0.7 | 1.1 | 1.3 | 1.5 | 2.50 |

Figure 5A:
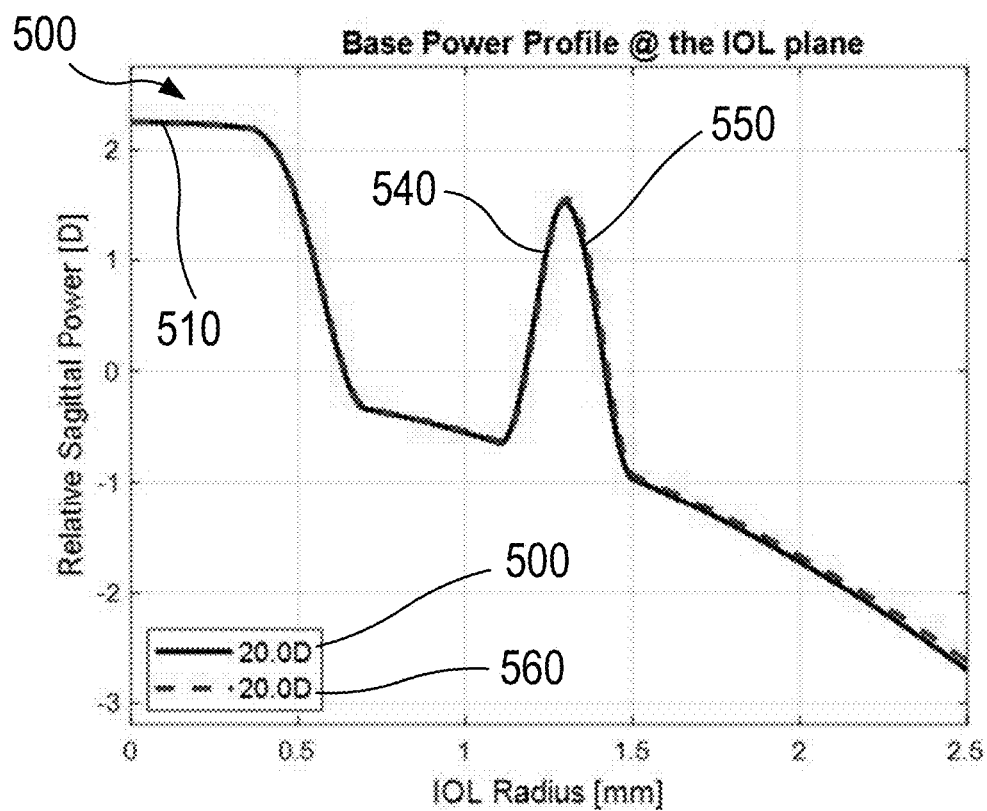
FIG. 5A depicts aspects of a wavefront power profile, according to embodiments of the present invention.

FIG. 5A depicts a wavefront power profile corresponding to the parameters provided in Table 4 added to the base (first) power profile of a standard negative spherical aberration lens. As shown in FIG. 5A, the power profile 500 does not contain abrupt changes in power or abrupt changes in curvature, such as those shown in FIG. 2A. The above parameters provide improved optical performance in low-light or night viewing conditions by avoiding or reducing side effects, including visual artifacts such as glare and halo, as well as best focus shifts and contrast sensitivity loss. As shown here, the power profile 500 provides an add power of 2.25 diopters in Zone 1, here labeled 510, and at the interface between Zone 4, here labeled 540, and Zone 5, here labeled 550. In some cases, the add power can be defined as the relative power with respect to the base power of the lens (e.g. base power of 20 diopters). The power profile 500 can include one or more zones having a continuous change in power from distance to near, that provides an Extended Depth of Focus (EDoF) behavior or performance. In some cases, such zones can include instances where the power changes when going from near focus to distance focus (e.g. Zone 2), when going from distance focus to near focus (e.g. Zone 4), and when going from near focus to distance focus (e.g. Zone 5). In some cases, such zones can be functional zones that contribute to generate smoother VA curves (EDoF).

Figure 5B:
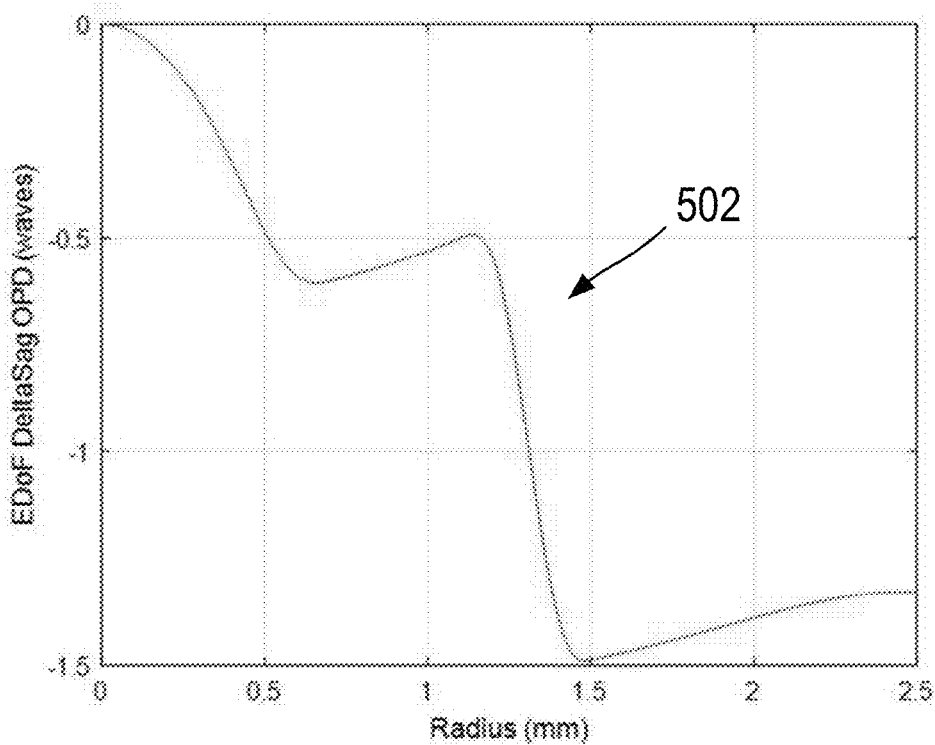
FIG. 5B depicts aspects of a refractive profile, according to embodiments of the present invention.

FIG. 5B depicts aspects of a refractive profile corresponding to Table 4. The Extended Depth of Focus (EDoF) DeltaSag Optical Path Difference (OPD) depicted here corresponds to the surface shape of a lens, where the base curvature has been removed. In some cases, the base curvature is spherical. In some cases, the base curvature is aspherical. The EDoF DeltaSag OPD can refer to the amount of curvature or sag that is added to a base curvature. In some cases, this profile 502 shows how the lens surface can deviate from a base curvature, which may be a monofocal lens profile. As shown here, the profile 502 can correspond to a function that is differentiable, because there are no "corners" such as those depicted in FIG. 2B. Given a refractive lens profile that corresponds to the DeltaSag profile 502 illustrated in FIG. 5B, it is possible to generate a lens power profile using a ray tracing technique. Such a lens power profile 560 is depicted in FIG. 5A. As shown there, the lens power profile 560 closely approximates the power profile 500.

Figure 8A:
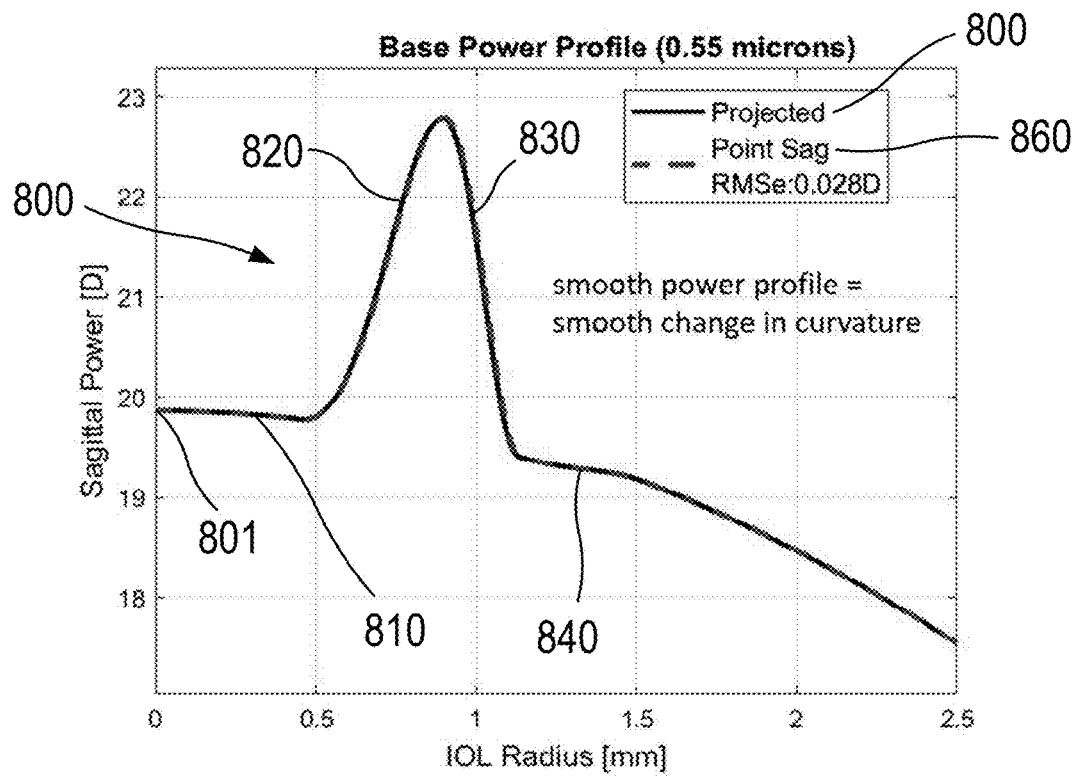
FIG. 8A depicts aspects of a wavefront power profile, according to embodiments of the present invention.
Figure 9A:
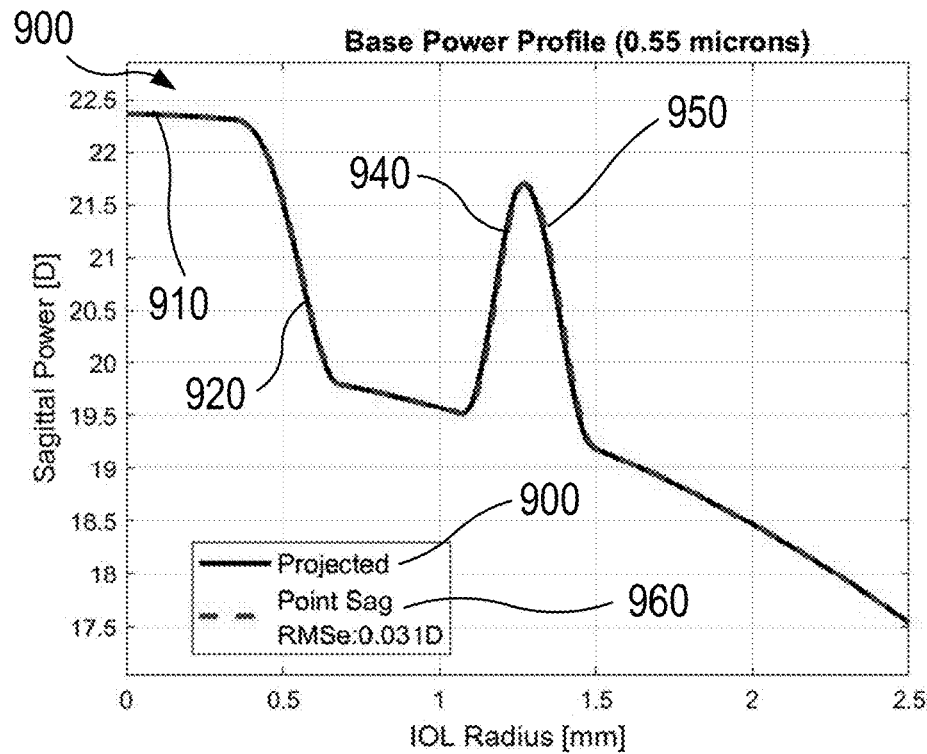
FIG. 9A depicts aspects of a power profile, according to embodiments of the present invention.

The profile depicted in FIG. 5A provides a center near design, aspects of which are also represented in FIG. 9A. It was discovered that having two zones of add power in a center near design is helpful in achieving the desired amount of near power, while maintaining a good performance for small pupils. In contrast, the center distance designs depicted in FIGS. 3A, 4A, 8A, and 10A can achieve the desired amount of near power using a single zone.

Figure 5C:
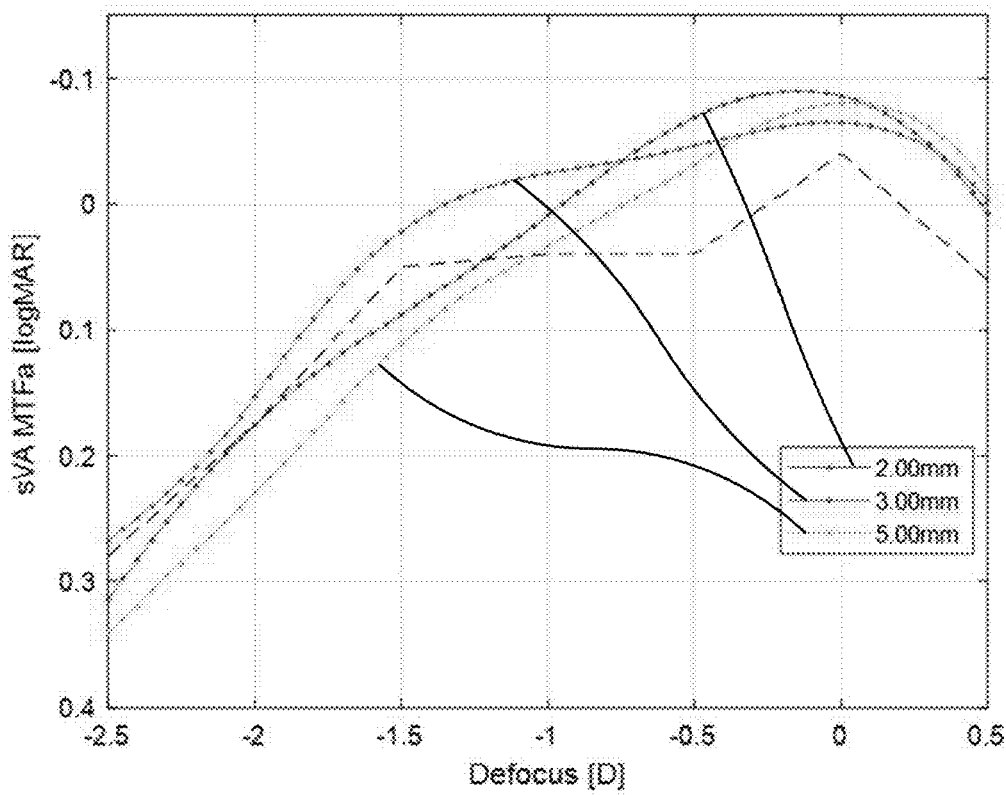
FIG. 5C depicts aspects of through focus Simulated Visual Acuity (sVA) area under the Modulation Transfer Function (MTFa) curves for a lens, according to embodiments of the present invention.

FIG. 5C depicts Simulated Visual Acuity (sVA) calculated from the area under the Modulation Transfer Function (MTFa) (see Alarcon et al. *Preclinical metrics to predict through-focus visual acuity for pseudophakic patients*, Biomedical Optics Express 7:1877-1888, 2016) curves for different pupil diameters corresponding to the parameters provided in Table 4. Compared to center distance profiles, center near profile 550 shows an improvement in distance sVA for 2 mm pupil diameters, although intermediate sVA is lower. By using one add power zone at the center followed by a second add power zone, the area of both zones can be reduced, compared to using a single zone, which results in lower pupil dependency.

According to some embodiments, it is possible to adjust the power and/or size of the zones, for example to increase the depth of focus for one or more pupil sizes. Table 4A below provides parameters for an exemplary wavefront power profile, according to embodiments of the present invention, as will be described below with reference to FIGS. 4D-4F.

TABLE 4A

|  | Zone 1 | Zone 2 | Zone 3 | Zone 4 | Zone 5 | Zone 6 |
|---|---|---|---|---|---|---|
| k | 1 | 2 | 3 | 4 | 5 | 6 |
| S (±0.25 D) | 2.25 | 2.25 | −0.25 | −0.25 | 3 | 0 |
| A (±0.25 D) | 0 | 2.50 | 0 | −3.25 | 3 | 0 |
| CosOrder | 1 | 1 | 1 | 1 | 1 | 1 |
| $rz_i$ (±0.1 mm) | 0.00 | 0.4 | 0.7 | 1.1 | 1.3 | 1.50 |
| $rz_e$ (±0.1 mm) | 0.4 | 0.7 | 1.1 | 1.3 | 1.5 | 2.50 |

Figure 5D:
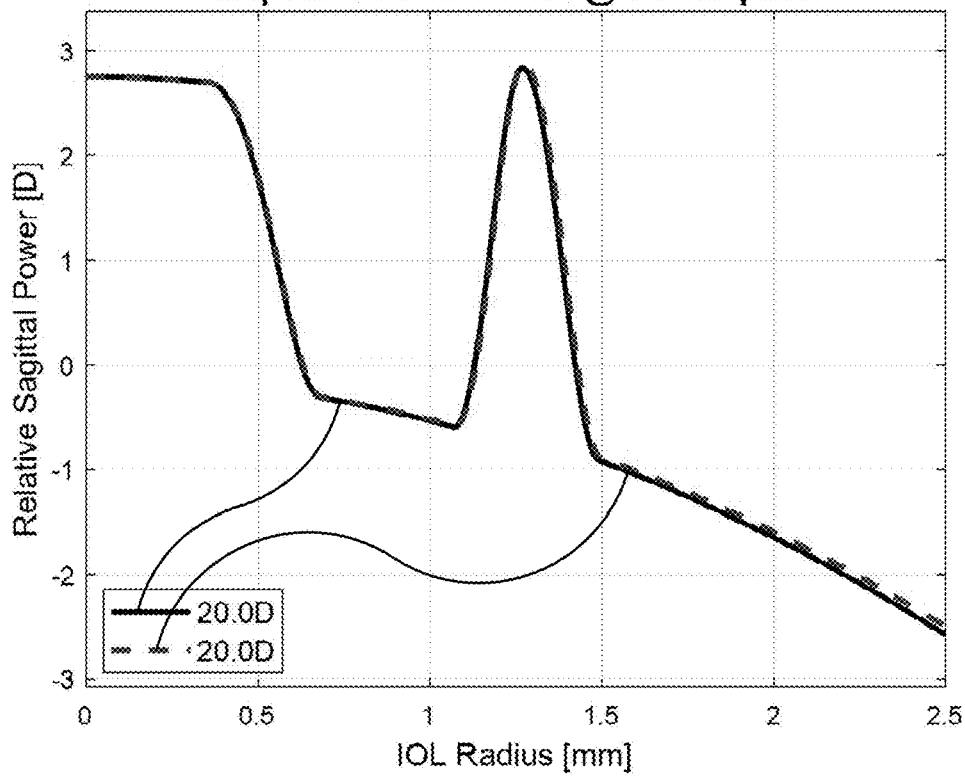
FIG. 5D depicts aspects of a wavefront power profile, according to embodiments of the present invention.
Figure 5E:
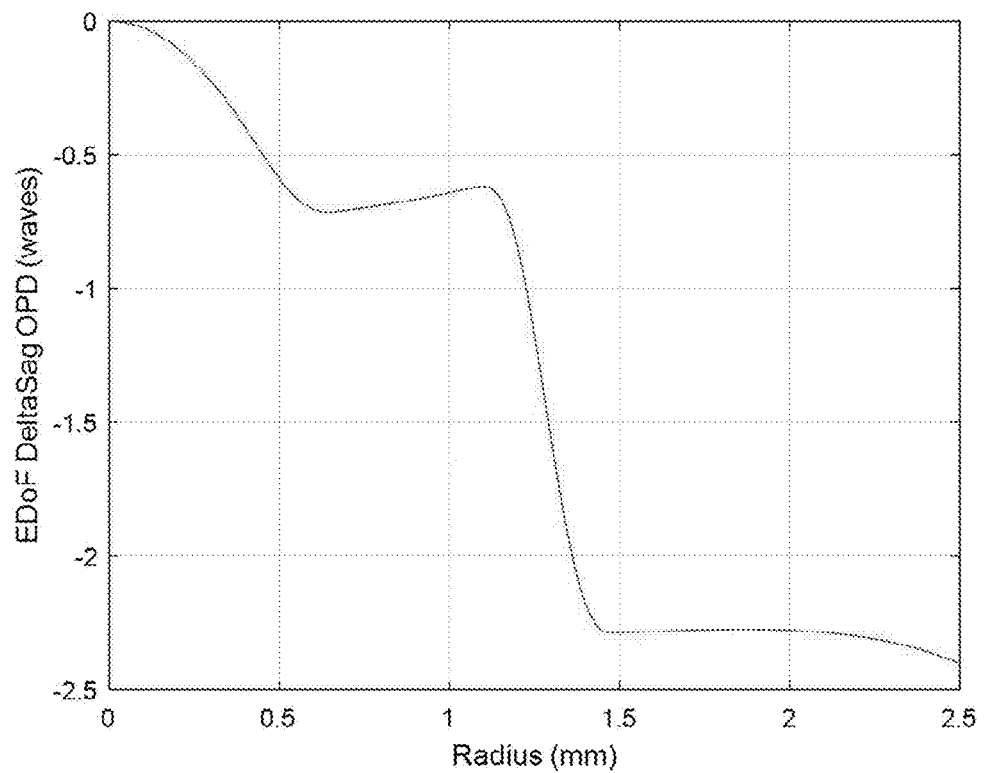
FIG. 5E depicts aspects of a refractive profile, according to embodiments of the present invention.
Figure 5F:
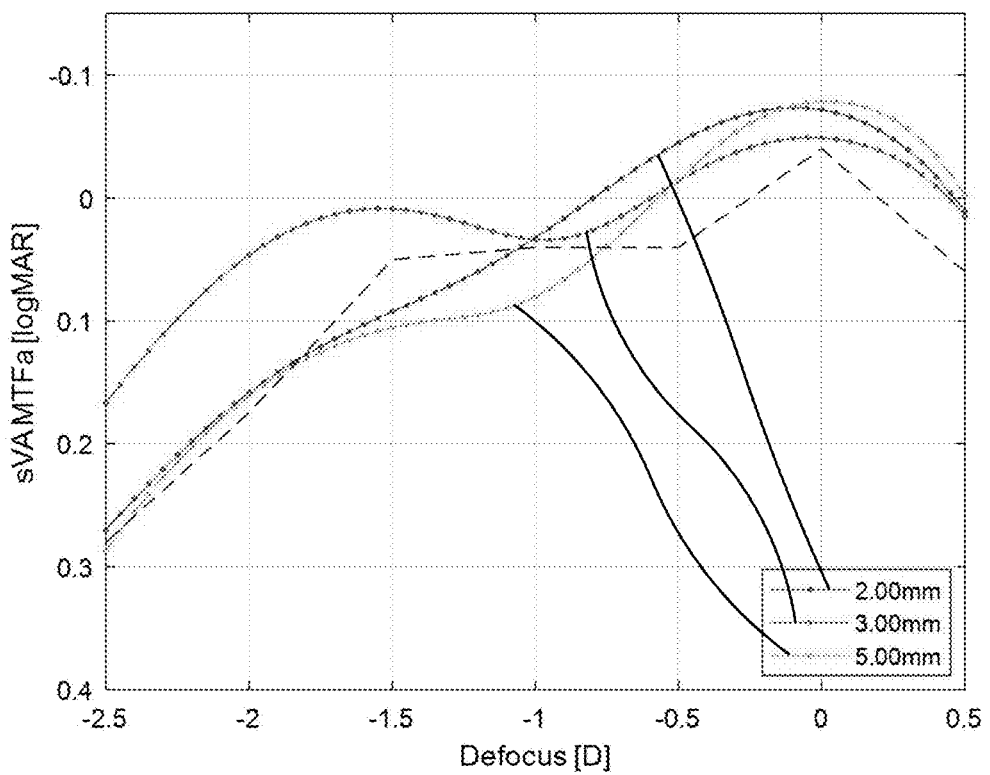
FIG. 5F depicts aspects of through focus Simulated Visual Acuity (sVA) area under the Modulation Transfer Function (MTFa) curves for a lens, according to embodiments of the present invention.

FIGS. 5D, 5E, and 5F correspond to Table 4A, and embody a design where the EDoF performance has been optimized for a maximum benefit at 3 mm pupil. In some cases, the relationship between FIGS. 5D, 5E, and 5F to Table 4A is similar to the relationship between FIGS. 2A, 2B, and 2C to Table 1, the relationship between FIGS. 3A, 3B, and 3C to Table 2, the relationship between FIGS. 4A, 4B, and 4C to Table 3, and/or the relationship between FIGS. 5A, 5B, and 5C to Table 4.

Figure 6A:
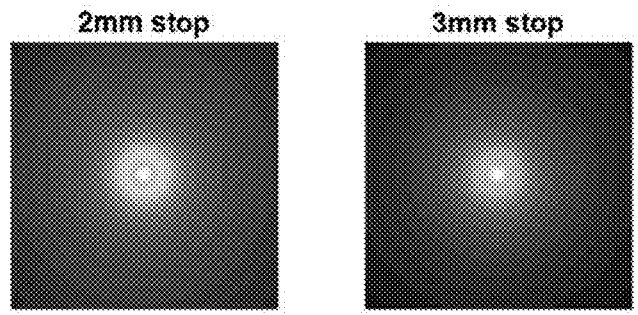
FIGS. 6A to 6D illustrates aspects of optical performance provided by power profiles, according to embodiments of the present invention.

FIG. 6A illustrates aspects of the optical performance provided by the power profile discussed above with regard to FIGS. 2A-2C. The stop values shown in these images can refer to the physical pupil.

Figure 6B:
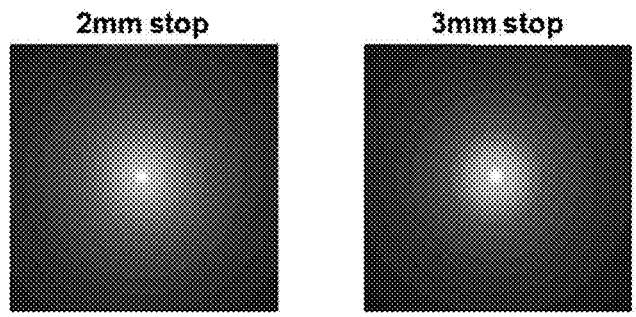

FIG. 6B illustrates aspects of the optical performance provided by the power profile discussed above with regard to FIGS. 3A-3D.

Figure 6C:
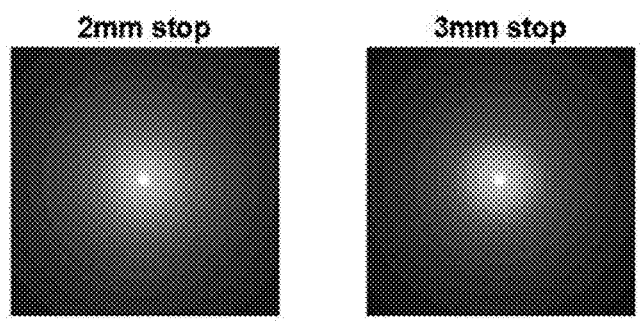

FIG. 6C illustrates aspects of the optical performance provided by the power profile discussed above with regard to FIGS. 4A-4D.

Figure 6D:
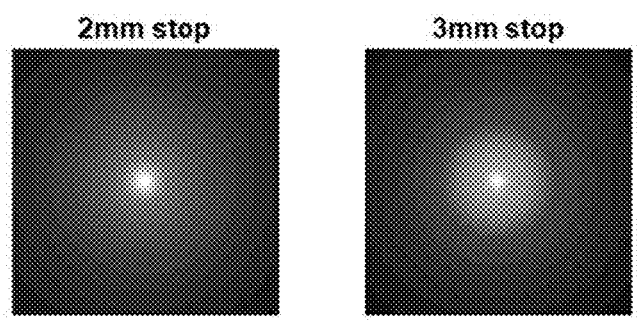

FIG. 6D illustrates aspects of the optical performance provided by the power profile discussed above with regard to FIGS. 5A-5C.

It can be seen that the power profile optical performance shown in FIG. 6C is improved relative to the power profile optical performance shown in FIGS. 6A and 6B. For example, the optical performance features depicted in FIG. 6C show better dysphotopsia performance (e.g. less halos and wide angle scatter for all pupils). FIG. 6D illustrates a more pupil independent performance (e.g. significantly better distance image quality for small pupils and no best focus shift for larger pupils). These images provide evidence for the lower halo performance, for example when comparing FIG. 6A at 2 mm versus the others. Embodiments of the present invention encompass similar plots for wide angle scatter.

Figure 7A:
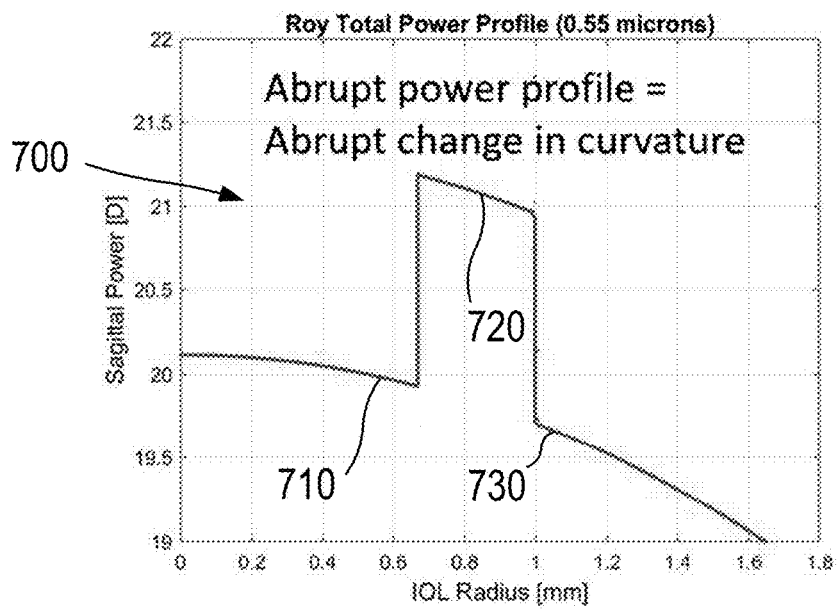
FIG. 7A depicts aspects of a power profile, according to embodiments of the present invention.

FIG. 7A depicts an exemplary power profile 700 according to embodiments of the present invention. As shown here, the power profile 700 contains abrupt changes in power, or abrupt changes in curvature (e.g. at radial distances 0.65 mm and 1.00 mm). The x-axis in FIG. 7A represents the sagittal power in diopters, whereas the x-axis in FIG. 2A represents the relative sagittal power in diopters (e.g. relative to a base power profile). In some embodiments, power profile 700 can be referred to as a theoretical or hypothetical power profile. Zone 1, here labeled 710, provides distance focus, Zone 2, here labeled 720, provides near focus, and Zone 3, here labeled 730, provides distance focus. As shown here, Zone 2 provides an add power of about 1.25 diopter. In some cases, the add power can be defined as the total power which also includes the base power of the lens (e.g. base power of 20 diopters). The power profile 700 does not include transition zones between the near and distance zones, as the power changes abruptly when going from the central Zone 1 (distance focus) to the peripheral Zone 2 (near focus), and when going from the peripheral Zone 2 (near focus) to the peripheral Zone 3 (distance focus).

Figure 7B:
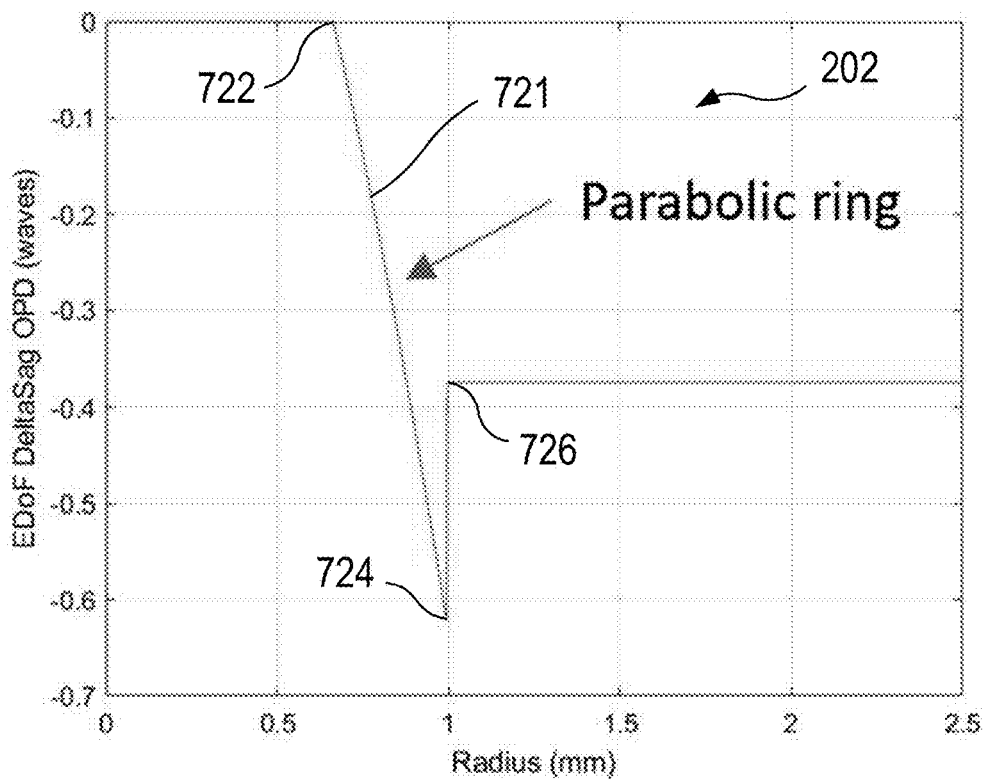
FIG. 7B depicts aspects of a refractive profile, according to embodiments of the present invention.

FIG. 7B depicts aspects of a refractive profile corresponding to FIG. 7A. The Extended Depth of Focus (EDoF) DeltaSag Optical Path Difference (OPD) depicted here corresponds to the surface shape of a lens, where the base curvature has been removed. In some cases, the base curvature is spherical. In some cases, the base curvature is aspherical. In some cases, a base curvature can have a monofocal design. The EDoF DeltaSag OPD can refer to the amount of curvature or sag that is added to a base curvature. In some cases, this profile 702 shows how the lens surface can deviate from a base curvature, which may be a monofocal lens profile. As shown here, the profile 702 can correspond to a function that is not differentiable, because of the "corners" 722, 724, and 726 corresponding to the outer borders of Zone 2, here labeled as 721.

In a distance focus zone, light that passes through this zone goes to a distance focus. In a near focus zone, light that passes through this zone goes to a near (or intermediate) focus. As noted above, in this embodiment the add power is about 1.25 D in the IOL plane and it extends from about 0.65 mm to about 1.00 mm in radial distance. There are no transition zones between the near and the distance zones and the power changes abruptly from one zone to the other (illustrated by vertical lines in the power profile).

FIG. 8A depicts an exemplary wavefront power profile 800 according to embodiments of the present invention. As shown here, the power profile 800 contains no abrupt changes in power or abrupt changes in curvature, such as those shown in FIG. 7A. As shown here, the power profile 800 provides an add power of about 3 diopters at the interface between Zone 2, here labeled 820, and Zone 3, here labeled 830. In some cases, the add power can be defined as the total power minus the base power of the lens (e.g. base power of 20 diopters). The power profile 800 includes zones with a smooth transition in power that create an EDoF effect, as the power changes when going from distance focus to near focus (e.g. Zone 2), and when going from near focus to distance focus (e.g. Zone 3). There are no abrupt changes in power between the near and the far zones, and the change in power between one zone and the other is achieved by a cosine function. The offset in Zones 1 and 4, here labeled 810 and 840, can operate to correct the peak of the MTF for all pupil sizes, and without being bound by any particular theory, it is believed that the offset also increases tolerancing to refractive errors in the positive side of the through focus.

Figure 10A:
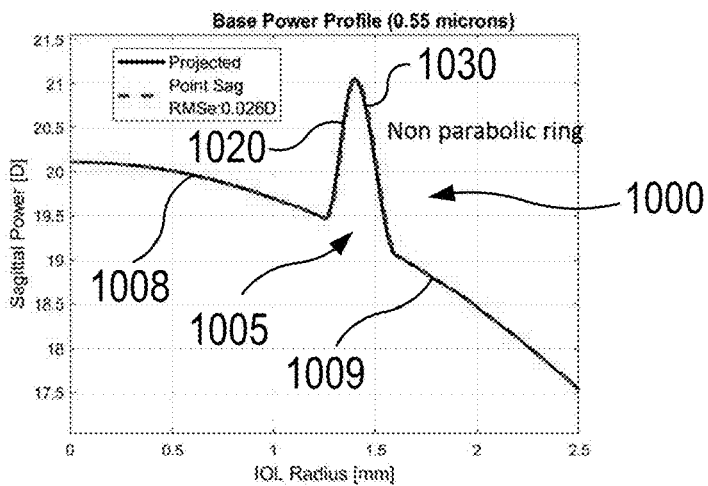
FIG. 10A depicts aspects of a power profile, according to embodiments of the present invention.

As depicted in FIG. 8A, a power profile 800 can have an offset 801 at a central location (e.g. where the sagittal power is slightly less than 20 diopters). The presence of the offset 801 can provide certain advantages. For example, the presence of the offset can help to provide a desired MTF profile. In some cases, the presence of the offset can operate to correct the peak, for the MTF, for different focal sizes. Relatedly, the offset can result in a similar or equivalent image quality peak for multiple different pupil sizes or for all pupil sizes. The presence of the offset can also help to provide good tolerance to refractive error. For example, when considering center distance embodiments such as those depicted in FIGS. 3A, 4A, and 8A and center near embodiments such as those depicted in FIGS. 5A and 9A. In some embodiments, the presence of the offset can operate to help correct the shifting power for other/bigger pupil sizes. FIG. 10A may depict aspects of a hybrid profile, which may be neither a center near nor a center distance profile.

In the embodiment depicted in FIG. 8A, the central power offset provides a relative negative power, which is about 0.25 diopters below 20 diopters (i.e. a −0.25 relative power to provide a sagittal power of about 19.75 diopters). In some cases, the offset can have a value of about −0.125 diopters. In some cases, the offset can have a value within a range from about −0.0625 diopters to about −0.25 diopters. In exemplary embodiments, there is no specific range, and this is connected to the rest of the profile, and it is used the balance the phase for a certain pupil size.

Figure 8B:
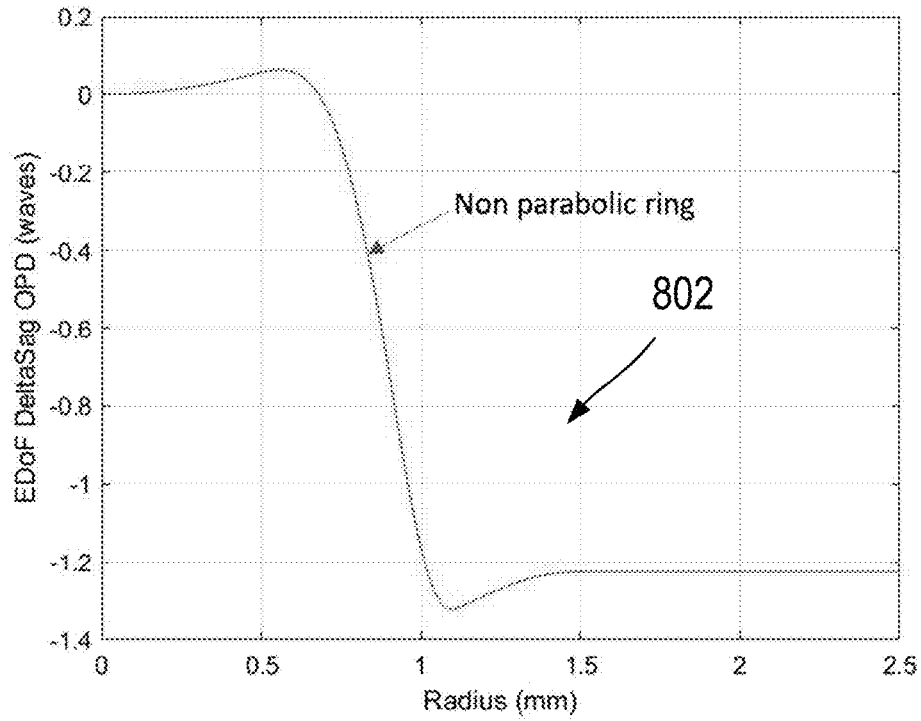
FIG. 8B depicts aspects of a refractive profile, according to embodiments of the present invention.

FIG. 8B depicts aspects of a refractive profile corresponding to FIG. 8A. The Extended Depth of Focus (EDoF) DeltaSag Optical Path Difference (OPD) depicted here corresponds to the surface shape of a lens, where the base curvature has been removed. In some cases, the base curvature is spherical. In some cases, the base curvature is aspherical. The EDoF DeltaSag OPD can refer to the amount of curvature or sag that is added to a base curvature. In some cases, this profile 802 shows how the lens surface can deviate from a base curvature, which may be a monofocal lens profile. As shown here, the profile 802 can correspond to a function that is differentiable, because there are no "corners" such as those depicted in FIG. 2B. Given a refractive lens profile that corresponds to the DeltaSag profile 802 illustrated in FIG. 8B, it is possible to generate a lens power profile using a ray tracing technique. Such a lens power profile 860 is depicted in FIG. 8A. As shown there, the lens power profile 860 closely approximates the power profile 800.

As shown in FIG. 8A, the power profile 800 (which can correspond to a prescription for a manufactured lens) has a central zone having a power of about 19.75 diopters which corresponds to a distance power, and as the profile extends toward the radial periphery, the sagittal power decreases slightly, before increasing in value to the point of the add power peak where the profile 800 reaches the interface between Zone 2, here labeled 820, and Zone 3, here labeled 830. In contrast, a monofocal design would provide a constant power value along the entirety of the radius. Peripheral to the add power peak (e.g. extending outward from the interface between Zone 2 and Zone 3) as the value of the radius increases, the sagittal power of the power profile decreases significantly and eventually returns to the slightly decreasing trajectory associated with the central portion of the power profile. This slightly decreasing trajectory can operate to compensate for a positive spherical aberration in a patient's eye. In other words, the base curvature can be designed to correct for or ameliorate spherical aberration in the patient's eye, such that the power peak of the lens provides an add power for the patient's eye, and the other portions of the lens provide a flat continuous power (e.g. on opposing sides of the power peak).

FIG. 9A depicts an exemplary power profile 900 according to embodiments of the present invention. The power profile 900 in FIG. 9A and the power profile 500 in FIG. 5A correspond to the same lens. Both power profiles represent power at the IOL plane. 0.55 microns is the wavelength for which the power is represented. As shown in FIG. 9A, the power profile 900 does not contain abrupt changes in power or abrupt changes in curvature, such as those shown in FIG. 7A. As shown here, the power profile 900 provides an add power of 2.40 diopters in Zone 1, here labeled 910, and at the interface between Zone 4, here labeled 940, and Zone 5, here labeled 950. In some cases, the add power can be defined as the total power which also includes the base power of the lens (e.g. base power of 20 diopters). The power profile 900 includes zones of smooth transition in power that improve the EDoF, as the power changes when going from near focus to distance focus (e.g. Zone 2, 920), when going from distance focus to near focus (e.g. Zone 4, 940), and when going from near focus to distance focus (e.g. Zone 5, 950).

Figure 9B:
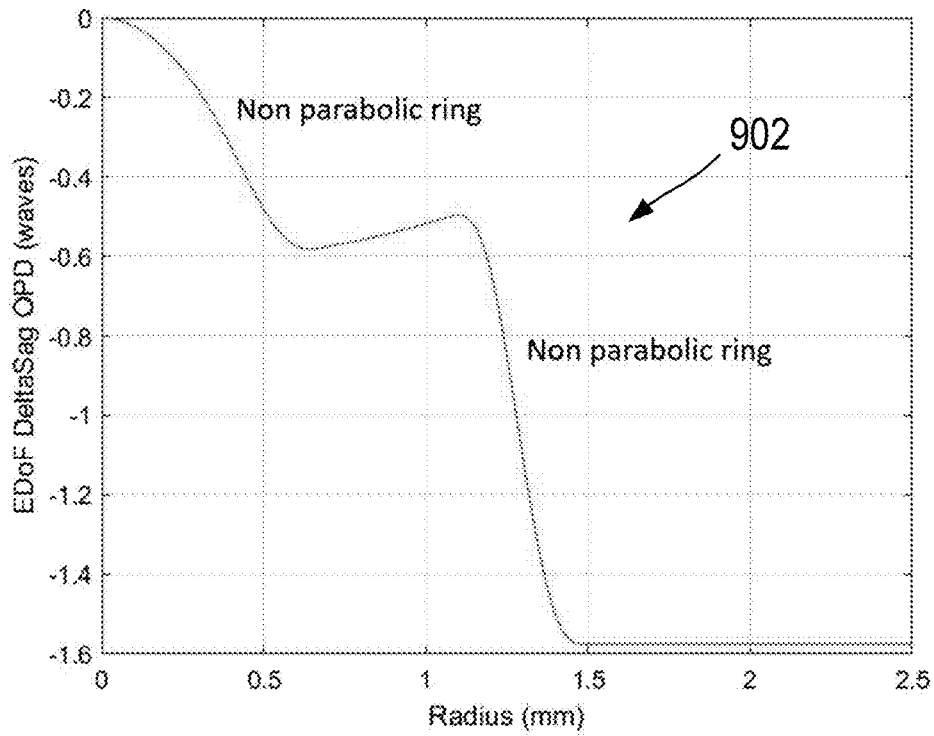
FIG. 9B depicts aspects of a refractive profile, according to embodiments of the present invention.

FIG. 9B depicts aspects of a refractive profile corresponding to FIG. 9A. The Extended Depth of Focus (EDoF) DeltaSag Optical Path Difference (OPD) depicted here corresponds to the surface shape of a lens, where the base curvature has been removed. In some cases, the base curvature is spherical. In some cases, the base curvature is aspherical. The EDoF DeltaSag can refer to the amount of curvature or sag that is added to a base curvature. In FIG. 9B and in other figures, DeltaSag can be provided in optical path difference (OPD) units for the design wavelength (waves). In some cases, the y axis can be changed to metric units (mm). Such conversions can be based on a formula where DeltaOPD(waves)=DeltaSag(mm)*(RI_lens−RI_aqueous)/0.55. In some cases, this profile 902 shows how the lens surface can deviate from a base curvature, which may be a monofocal lens profile. As shown here, the profile 902 can correspond to a function that is differentiable, because there are no "corners" such as those depicted in FIG. 7B. Given a refractive lens profile that corresponds to the DeltaSag profile 902 illustrated in FIG. 9B, it is possible to generate a lens power profile using a ray tracing technique. Such a lens power profile 960 is depicted in FIG. 9A. As shown there, the lens power profile 960 closely approximates the power profile 900.

FIG. 10A depicts an exemplary power profile 1000 according to embodiments of the present invention. As shown in FIG. 10A, the power profile 1000 does not contain abrupt changes in power or abrupt changes in curvature, such as those shown in FIG. 7A. As shown here, the power profile 1000 provides an add power of about 3 diopters at the interface between Zone 2, here labeled 1020, and Zone 3, here labeled 1030. In some cases, the add power can be defined as the total power which also includes the base power of the lens (e.g. base power of 20 diopters). The power profile 1000 includes zones of smooth transition in power that improves the EDoF, as the power changes when going from distance focus to near focus (e.g. Zone 2), and when going from near focus to distance focus (e.g. Zone 3).

Figure 10B:
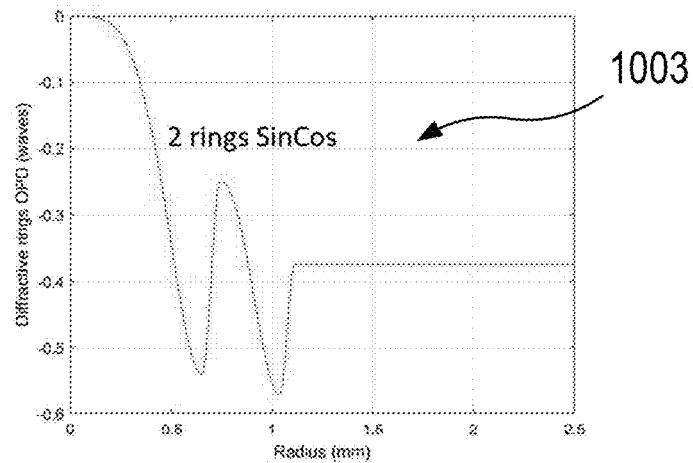
FIG. 10B depicts aspects of a diffractive profile which can be combined with a power profile, according to embodiments of the present invention.
Figure 10C:
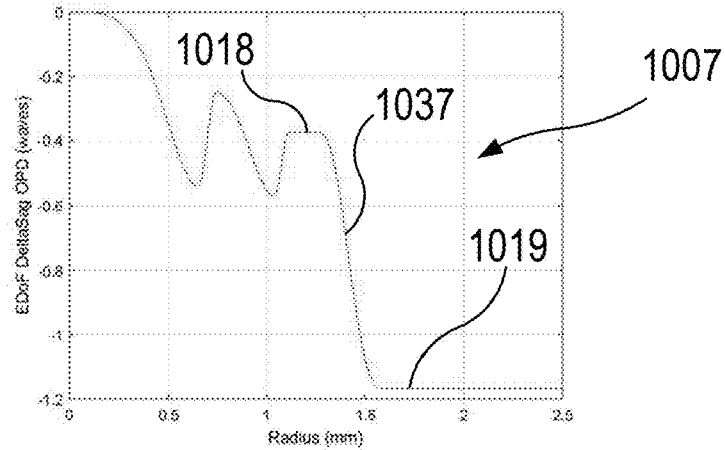
FIG. 10C depicts aspects of a combined profile, according to embodiments of the present invention.

FIG. 10B depicts aspects of a diffractive profile 1003 which can be combined with the power profile 1000 of FIG. 10A, to provide a hybrid profile 1007 or combined profile as shown in FIG. 10C. As shown here, zone 1030 depicted in FIG. 10A corresponds to zone 1037 depicted in FIG. 10C. With regard to FIG. 10A, in some embodiments, the base portions 1008 and 1009 correspond to a monofocal design, which are disposed on opposing sides of an add portion 1005 that provides a refractive add power. With regard to FIG. 10B, the diffractive profile provides two diffractive rings (e.g. 2 SinCos rings), which can be disposed centrally relative to the add portion 1005 shown in FIG. 10A. With regard to FIG. 10C, the DeltaSag curve contains two flat portions 1018, 1019, which correspond to the base portions 1008, 1009 shown in FIG. 10A, respectively. The diffractive profile 1003 shown in FIG. 10B has two rings, and operates to separate a wavefront into two wavefronts, creating in a sense a bifocal wavefront. As shown in FIG. 10C, the profile 1007 can correspond to a function that is differentiable, because there are no "corners" such as those depicted in FIG. 7B. In some embodiments, a profile can contain up to four diffractive rings or echelettes disposed centrally to a refractive add power portion or zone. In some cases, the incorporation of a diffractive feature in addition to the refractive feature can operate to provide enhanced performance over that which is provided by the refractive feature alone.

Figure 11:
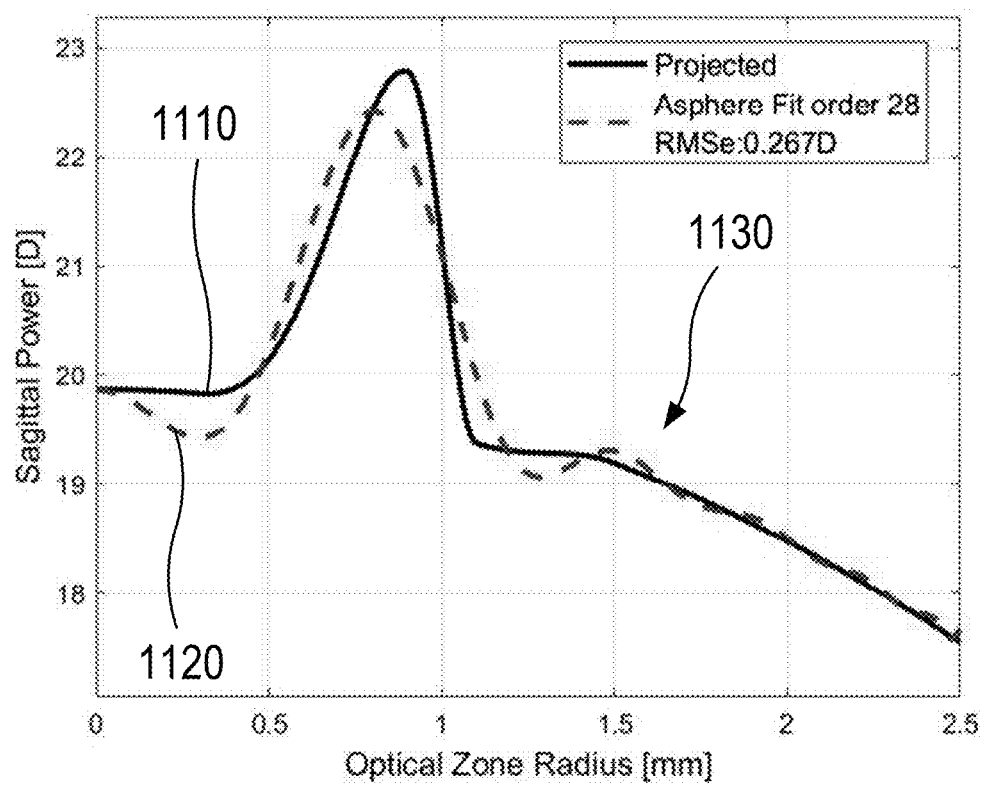
FIG. 11 illustrates aspects of a fitted curve and a projected curve, according to embodiments of the present invention.
Figure 11A:
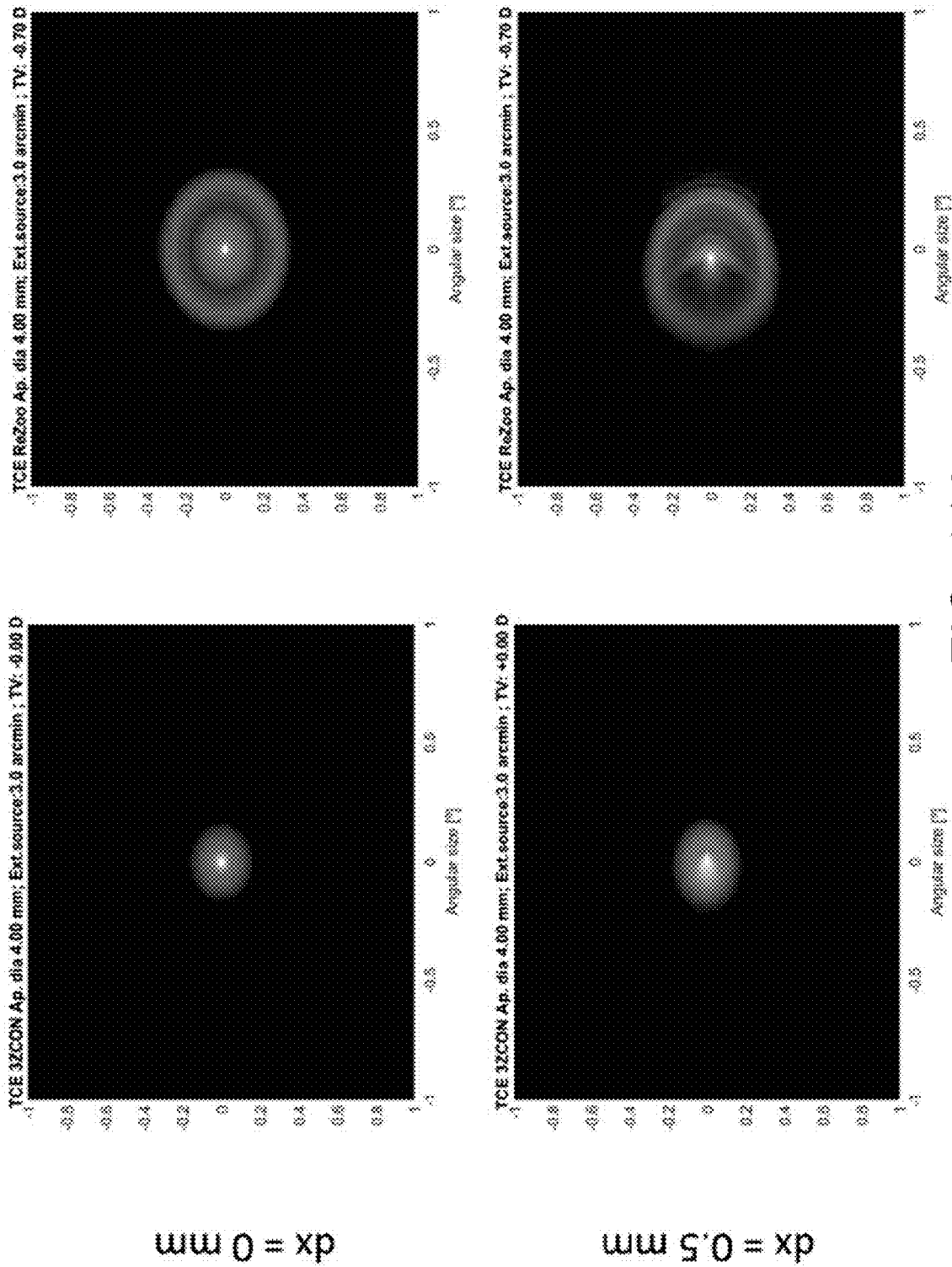
FIG. 11A depicts aspects of performance comparisons, according to embodiments of the present invention.

FIG. 11 illustrates how Runge's phenomenon can significantly change a power profile when the surface is fitted with a high order polynomial. As shown here, the fitted curve 1120 deviates from the projected curve 1110 in certain places. The fluctuations 1130 disposed peripherally to the add power zone 1105 represent low amplitude unwanted deformations caused by polynomial fitting (Runge's phenomenon), where the profile deviates from low amplitude shapes. The fitted curve 1120 (e.g. produced when the surface is fitted with a high order polynomial) has a lower residual, and toward the periphery, it begins deviating excessively from the projected curve 1110 (e.g. sagittal power profile of a desired surface). In this illustration, the order of the polynomial was chosen to give the best possible fit to the desired surface. FIG. 11A provides a comparison of the dysphotopsia profile of the design described in FIG. 11, curve 1110, and the Rezoom refractive multifocal IOL. FIG. 11A depicts halo with 0 and 0.5 mm of IOL decentration ($\gamma$=0.15), and illustrates that the exemplary design embodiments disclosed here can provide significantly less halos and are less sensitive to decentration (e.g. when compared with designs that have sharp changes in power).

Figure 12:
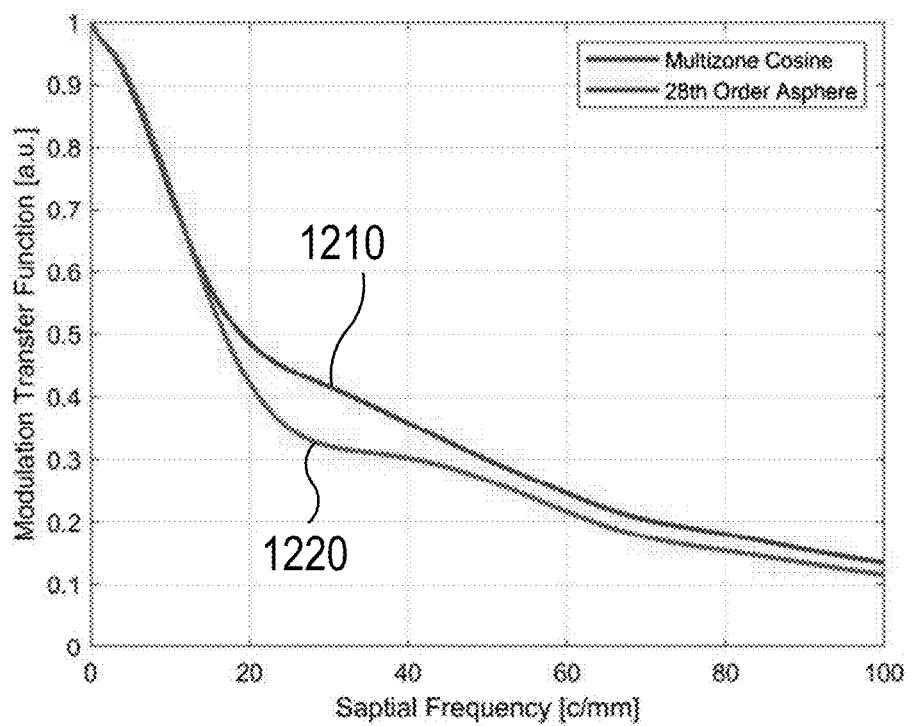
FIG. 12 depicts MTF features associated with a power profile, according to embodiments of the present invention.

FIG. 12 depicts MTF features associated with a power profile fitted with a cosine function embodiment (e.g. Equation 1) and a $28^{th}$ order asphere. In a multizone design embodiment the shape of each zone (e.g. wavefront power profile) can be described by a cosine function, that results in a final continuous surface. While this can provide advantages which are similar to those provided by a polynomial fitting in some instances (e.g. improved cosmetic appearance and reduced visual artifacts such as halo) it can also provide improved optical performance by allowing for a better control of the final design. FIG. 12 depicts a comparison between MTF curves for both a multizone cosine surface 1210 and a high order polynomial 1220. These curves correspond to the MTF for a 3 mm pupil. The multizone cosine label can refer to power a profile fitted with a cosine function (e.g. Equation 1), in this case the profile 1110 depicted in FIG. 11, which is also shown in FIG. 8A.

Figure 13:
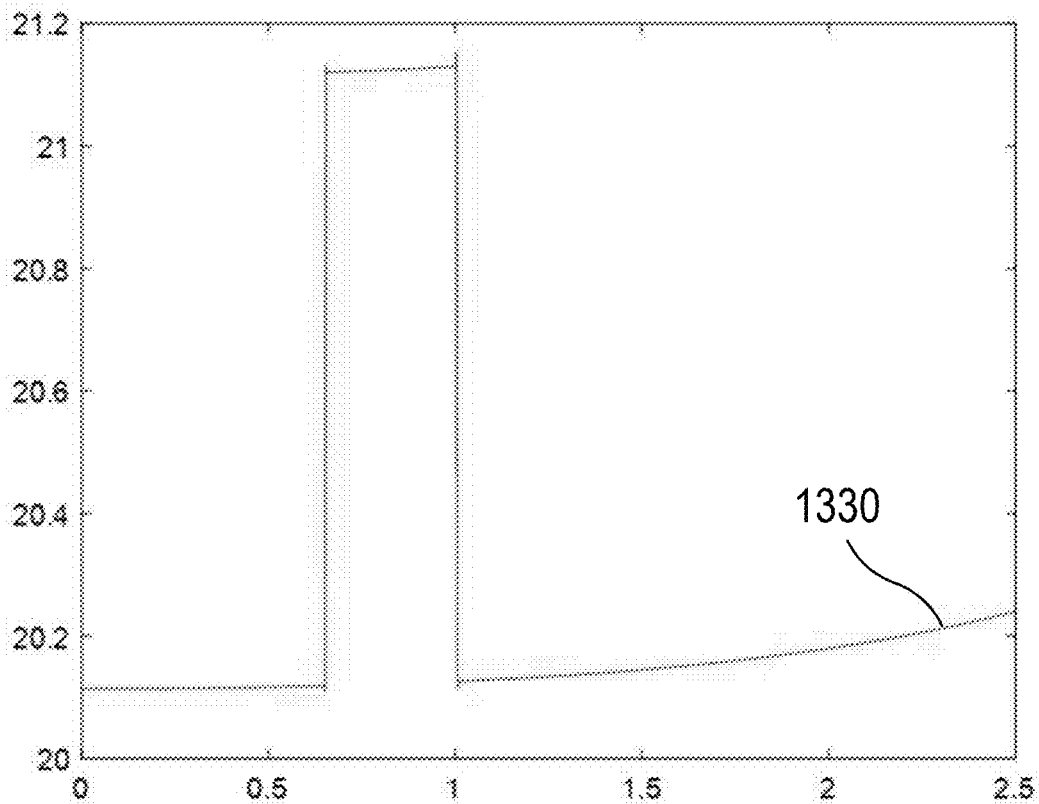
FIG. 13 depicts aspects of a power profile, according to embodiments of the present invention.

As noted above with reference to FIG. 7A for example, a profile can have a change in power from the zero radial position to the periphery due to an aspheric design of an IOL that matches the spherical aberration (SA) of a TECNIS IOL. If the lens would be described by spherical surfaces, the power profile would have a shape as shown in FIG. 13 with a smooth increase in power in the periphery 1330 due to the positive SA induced by a spherical IOL.

Figure 14:
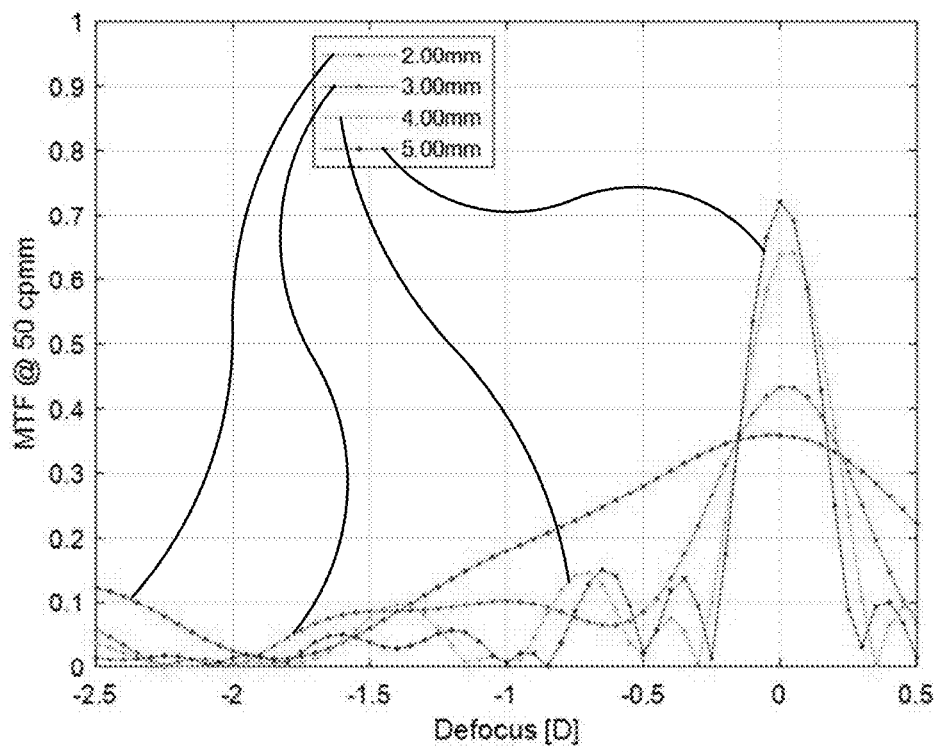
FIG. 14 depicts aspects of through focus MTF curves, according to embodiments of the present invention.
Figure 15:
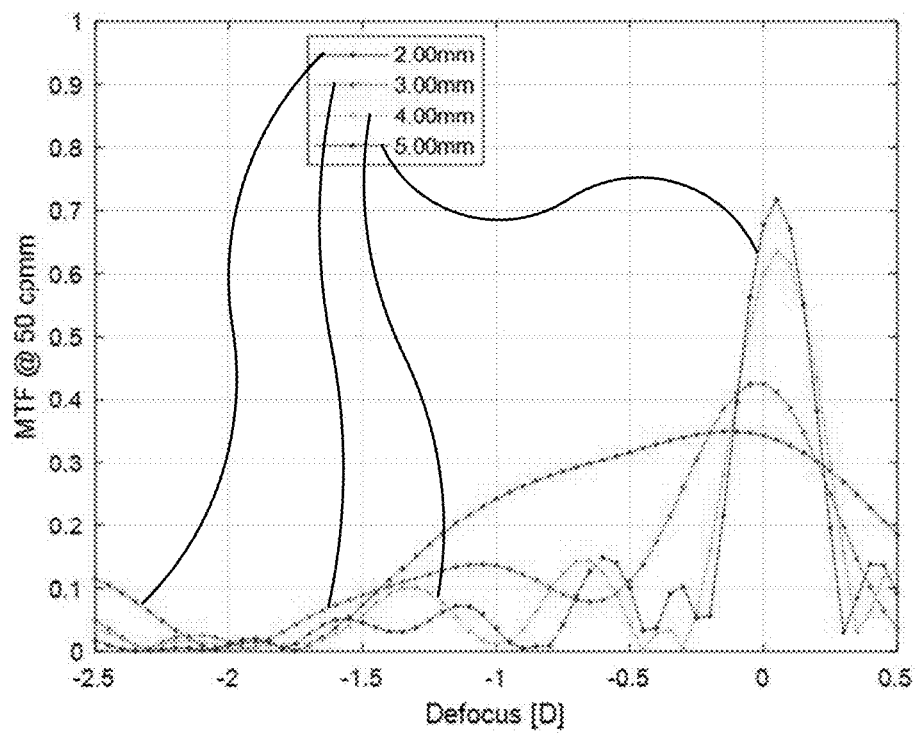
FIG. 15 depicts aspects of through focus MTF curves, according to embodiments of the present invention.

FIGS. 14 and 15 illustrate through focus MTF curves for different pupil sizes (from 2 mm to 5 mm) for a design that is similar to the design described in FIG. 8A. The difference between FIG. 14 and FIG. 15 is that the offset in Zones 1 and 4 is zero in FIG. 8A which results in a difference in best focus position between the difference pupil sizes (particularly between 5 mm and 3 mm and between 5 mm and 2 mm). The offset of Zones 1 and 4 is relative to the base power of the lens (e.g. 20 D).

Variations of wavefront power profiles, such as those depicted in FIG. 3A, can have value ranges for their initial/starting and final/ending zone boundaries or edges. Exemplary wavefront power profile range values are provided below in Table 5, Table 6, Table 7 and Table 8.

TABLE 5

|  | Zone 1 | Zone 2 | Zone 3 | Zone 4 | Zone 5 |
|---|---|---|---|---|---|
| k | 1 | 2 | 3 | 4 | 5 |
| S min (±0.25 D) | −2 | −2 | −2 | −2 | −2 |
| S max (±0.25 D) | 0 | 6 | 6 | 2 | 2 |
| A min (±0.25 D) | −8 | −8 | −8 | −4 | −4 |
| A max (±0.25 D) | 2 | 8 | 8 | 8 | 4 |
| CosOrder min | 1 | 1 | 1 | 1 | 1 |
| CosOrder max | 3 | 3 | 3 | 3 | 3 |
| $rz_i$ min (±0.1 mm) | 0.0 | 0.2 | 0.4 | 0.6 | 0.8 |
| $rz_i$ max (±0.1 mm) | 1 | 2 | 3 | End of the lens | End of the lens |
| $rz_e$ min (±0.1 mm) | 0.2 | 0.4 | 0.6 | 0.8 | 1.0 |
| $rz_e$ max (±0.1 mm) | 2 | 3 | 4 | End of the lens | End of the lens |

TABLE 6

|  | Zone 1 | Zone 2 | Zone 3 | Zone 4 | Zone 5 |
|---|---|---|---|---|---|
| k | 1 | 2 | 3 | 4 | 5 |
| S min (±0.25 D) | −0.5 | −0.5 | −0.5 | −0.5 | −0.5 |
| S max (±0.25 D) | 0 | 4.5 | 4.5 | 1 | 1 |
| A min (±0.25 D) | −5 | −5 | −5 | −1.5 | −1.5 |
| A max (±0.25 D) | 0.5 | 5 | 5 | 5 | 1.5 |
| CosOrder min | 1 | 1 | 1 | 1 | 1 |
| CosOrder max | 3 | 3 | 3 | 3 | 3 |
| $rz_i$ min (±0.1 mm) | 0.0 | 0.3 | 0.6 | 0.9 | 1.0 |
| $rz_i$ max (±0.1 mm) | 0.0 | 1.0 | 1.5 | 2.0 | End of the lens |
| $rz_e$ min (±0.1 mm) | 0.3 | 0.6 | 0.9 | 1.0 | 1.0 |
| $rz_e$ max (±0.1 mm) | 1.0 | 1.5 | 2.0 | End of the lens | End of the lens |

In some cases, it is possible to provide a central add power that is 0 or less than 0. Such a profile, which may be referred to as a small pupil design profile, can be defined by 7 zones as shown below.

TABLE 7

|  | Zone 1 | Zone 2 | Zone 3 | Zone 4 | Zone 5 | Zone 6 | Zone 7 |
|---|---|---|---|---|---|---|---|
| k | 1 | 2 | 3 | 4 | 5 | 6 | 7 |
| S min (±0.25 D) | −2 | −2 | −2 | −2 | −2 | −2 | −2 |
| S max (±0.25 D) | 6 | 6 | 6 | 6 | 6 | 2 | 2 |
| A min (±0.25 D) | −8 | −8 | −8 | −8 | −8 | −4 | −4 |
| A max (±0.25 D) | 8 | 8 | 8 | 8 | 8 | 8 | 4 |
| CosOrder min | 1 | 1 | 1 | 1 | 1 | 1 | 1 |
| CosOrder max | 3 | 3 | 3 | 3 | 3 | 3 | 3 |
| $rz_i$ min (±0.1 mm) | 0.0 | 0.2 | 0.4 | 0.6 | 0.8 | 1.0 | 1.2 |
| $rz_i$ max (±0.1 mm) | 1 | 2 | 3 | 4 | End of the lens | End of the lens | End of the lens |
| $rz_e$ min (±0.1 mm) | 0.2 | 0.4 | 0.6 | 0.8 | 1.0 | 1.2 | 1.4 |
| $rz_e$ max (±0.1 mm) | 2 | 3 | 4 | End of the lens | End of the lens | End of the lens | End of the lens |

TABLE 8

|  | Zone 1 | Zone 2 | Zone 3 | Zone 4 | Zone 5 | Zone 6 | Zone 7 |
|---|---|---|---|---|---|---|---|
| k | 1 | 2 | 3 | 4 | 5 | 6 | 7 |
| S min (±0.25 D) | −0.5 | −0.5 | −0.5 | −0.5 | −0.5 | −0.5 | −0.5 |
| S max (±0.25 D) | 4.5 | 4.5 | 4.5 | 4.5 | 4.5 | 1 | 1 |
| A min (±0.25 D) | −5 | −5 | −5 | −5 | −5 | −1.5 | −1.5 |
| A max (±0.25 D) | 5 | 5 | 5 | 5 | 5 | 5 | 1.5 |
| CosOrder min | 1 | 1 | 1 | 1 | 1 | 1 | 1 |
| CosOrder max | 3 | 3 | 3 | 3 | 3 | 3 | 3 |
| $rz_i$ min (±0.1 mm) | 0.0 | 0.2 | 0.4 | 0.6 | 0.8 | 1.0 | 1.2 |
| $rz_i$ max (±0.1 mm) | 0.0 | 1.0 | 1.5 | 2.0 | End of the lens | End of the lens | End of the lens |
| $rz_e$ min (±0.1 mm) | 0.2 | 0.4 | 0.6 | 0.8 | 1.0 | 1.2 | 1.4 |
| $rz_e$ max (±0.1 mm) | 1.0 | 1.5 | 2.0 | End of the lens | End of the lens | End of the lens | End of the lens |

Extended Depth of Focus

Embodiments herein disclosed also relate to lenses having a refractive profile that provides a continuous power progression to provide an extended depth of focus (EDoF). The power progression can be imposed on the anterior or on the posterior lens surface. Defining the sagittal optical power to vary as a cosine function of the radial position creates an extension of the depth of focus without discrete focusing positions, which results in a smoother through focus behavior.

Methods of manufacture for lenses and lens profiles as disclosed herein, as well as methods of treatment utilizing said lenses may include techniques described in, e.g., U.S. Pat. No. 9,335,563, entitled "Multi-Ring Lens, Systems And Methods For Extended Depth Of Focus," which is hereby incorporated by reference.

Diffractive lenses can make use of a material having a given refractive index and a surface curvature which provide a refractive power. Diffractive lenses affect chromatic aberration. Diffractive lenses have a diffractive profile which confers the lens with a diffractive power or power profile that contributes to the overall depth of focus of the lens. The diffractive profile is typically characterized by a number of diffractive zones. When used for ophthalmic lenses these diffractive zones are typically annular lens zones, or echelettes, spaced about the optical axis of the lens. Each echelette may be defined by an optical zone, a transition zone between the optical zone and an optical zone of an adjacent echelette, and echelette geometry. The echelette geometry includes an inner and outer diameter and a shape or slope of the optical zone, a height or step height, and a shape of the transition zone. The surface area or diameter of the echelettes largely determines the diffractive power(s) of the lens and the step height of the transition between echelettes largely determines the light distribution between the different powers. Together, these echelettes form a diffractive profile. The diffractive profile affects ocular chromatic aberration. Chromatic aberration can be increased or decreased depending on the morphology of the echelettes that compose the diffractive profile. The modification of chromatic aberration can be at distance, intermediate, near and/or the complete range of vision provided by the diffractive profile.

A traditional multifocal diffractive profile on a lens may be used to mitigate presbyopia by providing two or more optical powers, for example, one for near vision and one for far vision. The hybrid diffractive/refractive lenses disclosed herein provide an extended depth of focus across a range of optical powers. The lenses may take the form of an intraocular lens placed within the capsular bag of the eye, replacing the original lens, or placed in front of the natural crystalline lens. The lenses may also be in the form of a contact lens.

In specific embodiments, the refractive profile and diffractive profile may be applied to the same side of the lens (e.g., both on a posterior surface of the lens, or both on an anterior surface of the lens); or may be applied on opposite surfaces (e.g., with the diffractive profile on the posterior surface and the refractive power-progressive profile on the anterior surface).

In accordance with various embodiments, lens surfaces as disclosed herein may be applied to any suitable existing IOL design. Suitable IOL designs can include toric, monofocal, multifocal, extended range of vision, and refractive-diffractive lenses, and combinations thereof. In some cases, with suitable translation to a corresponding optical plane, methods of determining a lens shape can also be applied to corneal refractive procedures. In alternative embodiments, designs herein disclosed may also be applied to any suitable aspheric optical surface, e.g. IOLs, corneal inlays, and corneal onlays.

In various embodiments, diffractive designs can be added to lenses generated according to the techniques described above. Suitable diffractive designs can include designs for controlling chromatic aberration, to generate multifocal effects, and/or to extend depth of focus.

Computational Systems And Methods

Figure 16:
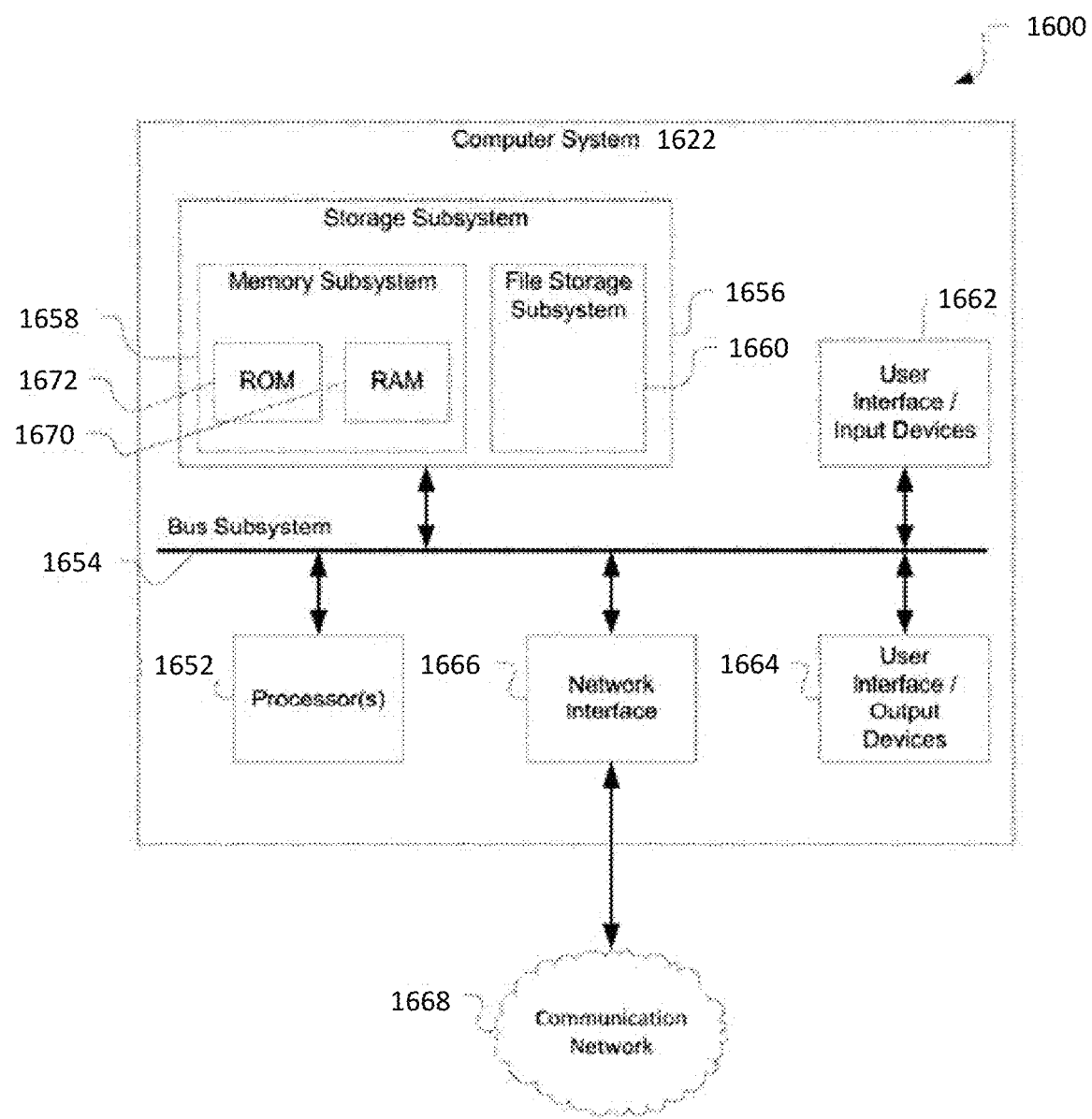
FIG. 16 depicts aspects of a computing environment, according to embodiments of the present invention.

FIG. 16 is a simplified block diagram of an exemplary computing environment 1600 that may be used by systems for generating the lens surfaces and other optical or wavefront features of the present disclosure. Computer system 1600 typically includes at least one processor 1652 which may communicate with a number of peripheral devices via a bus subsystem 1654. These peripheral devices may include a storage subsystem 1656 comprising a memory subsystem 1658 and a file storage subsystem 1660, user interface input devices 1662, user interface output devices 1664, and a network interface subsystem 1666. Network interface subsystem 1666 provides an interface to outside networks 1668 and/or other devices. In some cases, some portion of the above-referenced subsystems may be available in a diagnostics device capable of measuring the biometric inputs required for calculating attributes such as base power.

User interface input devices 1662 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 1662 will often be used to download a computer executable code from a tangible storage media embodying any of the methods of the present invention. In general, use of the term "input device" is intended to include a variety of conventional and proprietary devices and ways to input information into computer system 1622.

User interface output devices 1664 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 1622 to a user.

Storage subsystem 1656 can store the basic programming and data constructs that provide the functionality of the various embodiments of the present invention. For example, a database and modules implementing the functionality of the methods of the present invention, as described herein, may be stored in storage subsystem 1656. These software modules are generally executed by processor 1652. In a distributed environment, the software modules may be stored on a plurality of computer systems and executed by processors of the plurality of computer systems. Storage subsystem 1656 typically comprises memory subsystem 1658 and file storage subsystem 1660. Memory subsystem 1658 typically includes a number of memories including a main random access memory (RAM) 1670 for storage of instructions and data during program execution.

Various computational methods discussed above, e.g. with respect to generating a lens or refractive surface, may be performed in conjunction with or using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. All features of the described systems and devices are applicable to the described methods mutatis mutandis, and vice versa.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of skill in the art.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All references, including patent filings (including patents, patent applications, and patent publications), scientific journals, books, treatises, technical references, and other publications and materials discussed in this application, are incorporated herein by reference in their entirety for all purposes.

Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

While the above provides a full and complete disclosure of exemplary embodiments of the present invention, various modifications, alternate constructions and equivalents may be employed as desired. Consequently, although the embodiments have been described in some detail, by way of example and for clarity of understanding, a variety of modifications, changes, and adaptations will be obvious to those of skill in the art. Accordingly, the above description and illustrations should not be construed as limiting the invention, which can be defined by the appended claims.

Embodiments

Embodiment 1. A method of fabricating an intraocular lens, the method comprising:
 characterizing a first wavefront power profile corresponding to a theoretical lens;
 processing the first wavefront power profile with a cosine transformation to obtain a second wavefront power profile;
 determining a refractive profile based on the second wavefront power profile; and
 fabricating the intraocular lens based on the refractive profile.

Embodiment 2. The method of embodiment 1, wherein the first wavefront power profile comprises a first zone, a second zone disposed peripherally to the first zone, and a third zone disposed peripherally to the second zone.

Embodiment 3. The method of embodiment 2, wherein the cosine transformation operates to determine an optical power P(r) that varies as a cosine function of radial position inside each of the first, second, and third zones, according to a formula as follows:

$$P(r) = S - A(-1)^{CosOrder} * \left[ \frac{-1}{2} + \frac{1}{2} \cos\left[ \pi \left[ \frac{r^2 - rz_i^2}{rz_e^2 - rz_i^2} \right] \right]^{CosOrder} \right]$$

wherein A is an amplitude that is defined as a difference between a starting and a final sagittal power within each zone, S is a starting sagittal power of each zone, $rz_i$ and $rz_e$ are respectively starting (initial) and final radial coordinates of each zone, and Cos Order defines the power exponent of the cosine function.

Embodiment 4. The method of embodiment 3, wherein the amplitude A is provided in units of diopters.

Embodiment 5. The method of embodiment 3, wherein the starting sagittal power is provided in units of diopters.

Embodiment 6. The method of embodiment 3, wherein the starting and final radial coordinates are provided in units of mm.

Embodiment 7. The method of embodiment 1, wherein the step of determining the refractive profile comprises processing the second wavefront power profile with an analytical transformation to obtain the refractive profile.

Embodiment 8. The method of embodiment 1, wherein the second wavefront power profile is continuous.

Embodiment 9. The method of embodiment 1, wherein the refractive profile is continuous and differentiable.

Embodiment 10. The method of embodiment 1, wherein the intraocular lens has a refractive shape that is based on the refractive profile.

Embodiment 11. The method of embodiment 1, wherein the second wavefront profile has a relative sagittal power value of zero at a radial position of zero.

Embodiment 12. The method of embodiment 1, wherein the second wavefront profile has a relative sagittal power value that is non-zero at a radial position of zero.

Embodiment 13. The method of embodiment 12, wherein the relative sagittal power value is at the radial position of zero is negative.

Embodiment 14. The method of embodiment 1, wherein the second wavefront power profile has a center near configuration.

Embodiment 15. The method of embodiment 1, wherein the second wavefront power profile has a center distance configuration.

Embodiment 16. The method of embodiment 1, wherein the intraocular lens comprises a diffractive shape.

Embodiment 17. The method of embodiment 2, wherein the first wavefront power profile further comprises a fourth zone disposed peripherally to the third zone, a fourth zone disposed peripherally to the third zone and a fifth zone disposed peripherally to the fourth zone, or a fourth zone disposed peripherally to the third zone, a fifth zone disposed peripherally to the fourth zone, and a sixth zone disposed peripherally to the fifth zone.

Embodiment 18. The method of embodiment 2, wherein each zone is defined by a starting sagittal power (S), a final sagittal power, a starting radial position ($rz_i$), and a final radial position of the zone ($rz_e$).

Embodiment 19. The method of embodiment 18, wherein the starting radial position ($rz_i$) of the first zone is zero.

Embodiment 20. The method of embodiment 1, wherein the second wavefront profile has a relative sagittal power value of zero at least at one radial position and a relative sagittal power value that is positive with a value between 0.1 and 5 D for at least at one radial position.

Embodiment 21. The method of embodiment 1, wherein the second wavefront profile has a relative sagittal power value that is negative (with a value between −0.05 and −2 D) at least at one radial position and a relative sagittal power value that is positive (with a value between 0.1 and 5 D) for at least at one radial position.

Embodiment 22. The method of embodiment 2, wherein the sagittal power of the first zone is positive with at least one additional zone with zero or negative relative sagittal power.

Embodiment 23. The method of embodiment 2, wherein the sagittal power of the first zone is zero or negative with at least one additional zone with positive relative sagittal power.

Embodiment 24. The method of embodiment 3, wherein the optical power $P_k(r)$ profile is combined with a spherical intraocular lens design.

Embodiment 25. The method of embodiment 3, wherein the optical power $P_k(r)$ profile is combined with an aspheric intraocular lens design.

Embodiment 26. The method of embodiment 3, wherein the optical power $P_k(r)$ profile is combined with an astigmatism correcting intraocular lens design.

Embodiment 27. The method of embodiment 2, wherein the optical power $P_k(r)$ profile is combined with a diffractive profile.

Embodiment 28. A computer system to generate a refractive shape for use in fabricating an intraocular lens, the computer system comprising:
  a processor;
  an electronic storage location operatively coupled with the processor; and
  processor executable code stored on the electronic storage location and embodied in a tangible non-transitory computer readable medium,
  wherein the processor executable code, when executed by the processor, causes the processor to generate the refractive shape by:
    characterizing a first wavefront power profile corresponding to a theoretical lens;
    processing the first wavefront power profile with a cosine transformation to obtain a second wavefront power profile; and
    determining the refractive profile based on the second wavefront power profile.

Embodiment 29. The computer system of embodiment 28, wherein the first wavefront power profile comprises a first zone, a second zone disposed peripherally to the first zone, and a third zone disposed peripherally to the second zone.

Embodiment 30. The computer system of embodiment 29, wherein the cosine transformation operates to determine an optical power $P_k(r)$ that varies as a cosine function of radial position inside each of the first, second, and third zones, according to a formula as follows:

$$P(r) = S - A(-1)^{CosOrder} * \left[ \frac{-1}{2} + \frac{1}{2} \cos\left[ \pi \left[ \frac{r^2 - rz_i^2}{rz_e^2 - rz_i^2} \right] \right]^{CosOrder} \right]$$

wherein $A_k$ is an amplitude that is defined as a difference between a starting and a final sagittal power within each zone, $S_k$ is a starting sagittal power of each zone, $rz_{ik}$ and $rz_{ek}$ are respectively starting (initial) and final radial coordinates of each zone, and CosOrderk defines the power exponent of the cosine function.

Embodiment 31. The computer system of embodiment 30, wherein the amplitude $A_k$ is provided in units of diopters.

Embodiment 32. The computer system of embodiment 30, wherein the starting sagittal power is provided in units of diopters.

Embodiment 33. The computer system of embodiment 30, wherein the starting and final radial coordinates are provided in units of mm.

Embodiment 34. The computer system of embodiment 28, wherein the step of determining the refractive profile comprises processing the second wavefront power profile with an analytical transformation to obtain the refractive profile.

Embodiment 35. The computer system of embodiment 28, wherein the second wavefront power profile is continuous.

Embodiment 36. The computer system of embodiment 28, wherein the refractive profile is continuous and differentiable.

Embodiment 37. The computer system of embodiment 28, wherein the intraocular lens has a refractive shape that is based on the refractive profile.

Embodiment 38. The computer system of embodiment 28, wherein the second wavefront profile has a relative sagittal power value of zero at a radial position of zero.

Embodiment 39. The computer system of embodiment 28, wherein the second wavefront profile has a relative sagittal power value that is non-zero at a radial position of zero.

Embodiment 40. The computer system of embodiment 39, wherein the relative sagittal power value is at the radial position of zero is negative.

Embodiment 41. The computer system of embodiment 28, wherein the second wavefront power profile has a center near configuration.

Embodiment 42. The computer system of embodiment 28, wherein the second wavefront power profile has a center distance configuration.

Embodiment 43. The computer system of embodiment 28, wherein the intraocular lens comprises a diffractive shape.

Embodiment 44. The computer system of embodiment 29, wherein the first wavefront power profile further comprises a fourth zone disposed peripherally to the third zone, a fourth zone disposed peripherally to the third zone and a fifth zone disposed peripherally to the fourth zone, or a fourth zone disposed peripherally to the third zone, a fifth zone disposed peripherally to the fourth zone, and a sixth zone disposed peripherally to the fifth zone.

Embodiment 45. The computer system of embodiment 29, wherein each zone is defined by a starting sagittal power ($S_k$), a final sagittal power, a starting radial position ($rz_{ik}$), and a final radial position of the zone ($rz_{ek}$).

Embodiment 46. The computer system of embodiment 45, wherein the starting radial position ($rz_{ik}$) of the first zone is zero.

Embodiment 47. The computer system of embodiment 28, wherein the second wavefront profile has a relative sagittal power value of zero at least at one radial position and a relative sagittal power value that is positive with a value between 0.1 and 5 D for at least at one radial position.

Embodiment 48. The computer system of embodiment 28, wherein the second wavefront profile has a relative sagittal power value that is negative (with a value between −0.05 and −2 D) at least at one radial position and a relative sagittal power value that is positive (with a value between 0.1 and 5 D) for at least at one radial position.

Embodiment 49. The computer system of embodiment 29, wherein the sagittal power of the first zone is positive with at least one additional zone with zero or negative relative sagittal power.

Embodiment 50. The computer system of embodiment 29, wherein the sagittal power of the first zone is zero or negative with at least one additional zone with positive relative sagittal power.

Embodiment 51. The computer system of embodiment 30, wherein the optical power $P_k(r)$ profile is combined with a spherical intraocular lens design.

Embodiment 52. The computer system of embodiment 30, wherein the optical power $P_k(r)$ profile is combined with an aspheric intraocular lens design.

Embodiment 53. The computer system of embodiment 30, wherein the optical power $P_k(r)$ profile is combined with an astigmatism correcting intraocular lens design.

Embodiment 54. The computer system of embodiment 29, wherein the optical power $P_k(r)$ profile is combined with a diffractive profile.

Embodiment 55. A method of generating a wavefront power profile for use in manufacture of an intraocular lens, the method comprising:
  obtaining a preliminary wavefront power profile corresponding to a theoretical lens; and
  processing the preliminary wavefront power profile with a cosine transformation to obtain the wavefront power profile.

Embodiment 56. A method of fabricating an intraocular lens, the method comprising:
  obtaining a wavefront power profile; and
  determining a refractive profile based on the wavefront power profile,
  wherein the step of determining the refractive profile comprises processing the wavefront power profile with an analytical transformation to obtain the refractive profile.

The invention claimed is:

1. An intraocular lens comprising: a refractive shape based on a refractive profile, wherein the refractive profile is based on a final wavefront power profile determined by adding to a first wavefront power profile a second wavefront power profile comprising a plurality of optical add powers at different radial positions, wherein the first wavefront power profile corresponds to a base power profile, wherein at least a first optical add power of the plurality of optical add powers follows the base power profile, and wherein the refractive profile has a maximum power peak at a radial position between approximately 0.5 mm and approximately 1.1 mm from an optical axis of the intraocular lens and wherein an entirety of the refractive profile is defined by a cosine function, wherein the final wavefront power profile has a starting sagittal power which extends from the center of the intraocular lens or its optical axis, which corresponds to the first wavefront power profile, and which decreases from an initial value in the range of 0 to −0.5 diopters.

2. The intraocular lens of claim 1, wherein at least one optical add power of the plurality of optical add powers of the second wavefront power profile comprises a peak sagittal power value which is an add power value in the range of 1.50 to 4.00, 2.50 to 4.00, 2.00 to 3.50, or 2.75 to 3.25 or 3.00 diopters above the first wavefront power profile.

3. The intraocular lens of claim 2, wherein the peak sagittal power value is located at the radial position of 0.5 mm to 1.5 mm, 0.6 to 1.2 mm, 0.8 to 1.0 mm, or 0.9 mm from the center of the intraocular lens or its optical axis.

4. The intraocular lens of claim 3, wherein in the final wavefront power profile, a transition from the first wavefront power profile into the final wavefront power profile comprises a continuous change in sagittal power from the first wavefront power profile to the peak sagittal power value determined by the cosine function.

5. The intraocular lens of claim 4, wherein in the final wavefront power profile, a transition from the first wavefront power profile into the final wavefront power profile comprises a continuous change in sagittal power from the peak sagittal power value to the first wavefront power profile determined by the cosine function.

6. The intraocular lens of claim 1, wherein the final wavefront power profile has at least one sagittal power in the range of −0.5 to 0.2 diopters.

7. The intraocular lens of claim 1, wherein the second wavefront power profile comprises an optical power that varies as a cosine transformation of radial position.

8. The intraocular lens of claim 7, wherein the second wavefront power profile comprises an optical power $P_k(r)$ that varies as the cosine function of radial position according to a formula as follows:

$$P_k(r) = S_k - A_k(-1)^{CosOrderk} * \left[ \frac{-1}{2} + \frac{1}{2}\cos\left[\pi\left[\frac{r^2 - rz_{ik}^2}{rz_{ek}^2 - rz_{ik}^2}\right]\right]^{CosOrderk} \right]$$

wherein $A_k$ is an amplitude that is defined as a difference between a starting and a final sagittal power, $S_k$ is a starting sagittal power, $rz_{ik}$ and $rz_{ek}$ are respectively initial and final radial coordinates, and CosOrderk defines the power exponent of the cosine function.

9. The intraocular lens of claim 1, wherein the maximum power peak is a relative sagittal power of 3 diopters±0.25 diopters.

* * * * *